US011861437B2

(12) United States Patent
Swager et al.

(10) Patent No.: US 11,861,437 B2
(45) Date of Patent: Jan. 2, 2024

(54) CHEMICAL AND PHYSICAL SENSING WITH A READER AND RFID TAGS

(71) Applicant: Massachusetts Institute of Technology, Cambridge, MA (US)

(72) Inventors: Timothy Manning Swager, Newton, MA (US); Joseph Michael Azzarelli, Cambridge, MA (US); Jens Bomholdt Ravnsbæk, Fredericia (DK); Katherine Andrea Mirica, Waltham, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/223,021

(22) Filed: Dec. 17, 2018

(65) Prior Publication Data

US 2019/0340480 A1    Nov. 7, 2019

Related U.S. Application Data

(63) Continuation of application No. 15/426,027, filed on Feb. 6, 2017, now Pat. No. 10,157,340, which is a
(Continued)

(51) Int. Cl.
*H04Q 5/22* (2006.01)
*G06K 19/07* (2006.01)
(Continued)

(52) U.S. Cl.
CPC ..... *G06K 19/0716* (2013.01); *G01N 33/0075* (2013.01); *G06K 19/0717* (2013.01);
(Continued)

(58) Field of Classification Search
CPC ........ G06K 19/0716; G06K 19/07788; G06K 19/0723; G06K 19/07749; G06K 19/0717;
(Continued)

(56) References Cited

U.S. PATENT DOCUMENTS 6,720,866 B1    4/2004    Sorrells et al.
7,040,139 B2    5/2006    Sunshine
(Continued)

FOREIGN PATENT DOCUMENTS

WO    2004/079644    9/2004

OTHER PUBLICATIONS

Office action mailed in European patent application 14880070.9 dated May 20, 2019.
(Continued)

*Primary Examiner* — Tanmay K Shah
(74) *Attorney, Agent, or Firm* — Honigman LLP

(57) ABSTRACT

A method of detecting a stimulus can include detecting an output from a radio frequency identification tag including a sensor. A smartphone-based sensing strategy can use chemiresponsive nanomaterials integrated into the circuitry of commercial Near Field Communication tags to achieve non-line-of-sight, portable, and inexpensive detection and discrimination of gas phase chemicals (e.g., ammonia, hydrogen peroxide, cyclohexanone, and water) at part-per-thousand and part-per-million concentrations.

15 Claims, 29 Drawing Sheets

Related U.S. Application Data continuation of application No. 14/528,856, filed on Oct. 30, 2014, now Pat. No. 9,563,833.

(60) Provisional application No. 61/897,613, filed on Oct. 30, 2013.

(51) Int. Cl.
| | |
|---|---|
| *G06K 19/077* | (2006.01) |
| *G01N 33/00* | (2006.01) |
| *G08C 17/02* | (2006.01) |
| *G01N 27/04* | (2006.01) |
| *G06F 3/01* | (2006.01) |

(52) U.S. Cl.
CPC ... *G06K 19/0723* (2013.01); *G06K 19/07749* (2013.01); *G06K 19/07788* (2013.01); *G08C 17/02* (2013.01); *G01N 27/04* (2013.01); *G06F 3/014* (2013.01)

(58) Field of Classification Search
CPC .... G01N 33/0075; G01N 27/04; G08C 17/02; G06F 3/014
USPC ........................................................ 340/10.4
See application file for complete search history.

(56) References Cited

U.S. PATENT DOCUMENTS

| | | | |
|---|---|---|---|
| 7,477,154 B2 | 1/2009 | Braunstein | |
| 7,648,844 B2 | 1/2010 | Srivastava et al. | |
| 7,769,038 B2 | 9/2010 | Naresh Batra | |
| 7,796,038 B2 | 9/2010 | Batra | |
| 7,999,673 B2 | 8/2011 | Killian | |
| 8,148,701 B2 | 4/2012 | Yoder | |
| 8,508,356 B2 | 8/2013 | Shuster | |
| 8,963,563 B2 | 2/2015 | Humbert et al. | |
| 9,052,263 B2 | 6/2015 | Potyrailo et al. | |
| 9,563,833 B2 | 2/2017 | Swager | |
| 2005/0022581 A1 | 2/2005 | Sunshine | |
| 2007/0176779 A1 | 8/2007 | Braunstein | |
| 2007/0285238 A1* | 12/2007 | Batra | G06K 19/0717 374/E1.004 |
| 2008/0129504 A1 | 6/2008 | Killian | |
| 2008/0135614 A1 | 6/2008 | Werner et al. | |
| 2009/0148857 A1 | 6/2009 | Srivastava et al. | |
| 2010/0207781 A1 | 8/2010 | Shuster | |
| 2011/0146400 A1 | 6/2011 | Humbert et al. | |
| 2011/0168902 A1 | 7/2011 | Yoder | |
| 2012/0116683 A1* | 5/2012 | Potyrailo | G01N 27/02 702/19 |
| 2012/0166095 A1* | 6/2012 | Potyrailo | G01N 27/3278 702/23 |
| 2012/0235690 A1 | 9/2012 | Potyrailo et al. | |
| 2013/0096369 A1* | 4/2013 | Folkers | A01K 29/005 600/33 |

OTHER PUBLICATIONS

Office action mailed in Japanese patent application 2016-527465 dated Jul. 16, 2019.
Office action mailed in European patent application 14880070.9 dated Mar. 31, 2020.
International Search Report and Written Opinion dated Jul. 13, 2015 in PCT/US14/63197.
Supplementary European Search Report dated Jul. 3, 2017 in EP 14880070.9.

* cited by examiner

Method 1

1. Cut — disrupt Circuit
2. Draw — sensor element
3. Expose to analyte
4. Measure $R_{sensor}$
5. Scan with smartphone

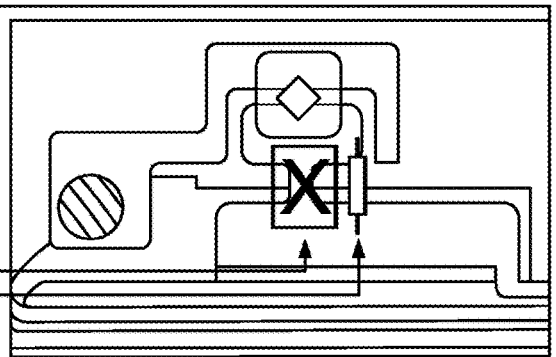

| $R_{sensor}$ | Tag | Phone Readout |
|---|---|---|
| <28 kOhm | Unreadable | tag detected! |
| >29 kOhm | Readable | Scan a tag... |

Turn-off ↓ / Turn-on ↑

FIG. 4A

Method 2

1. Draw — disrupt Circuit
2. Expose sensor element
3. Measure $R_{sensor}$
4. Scan with smartphone

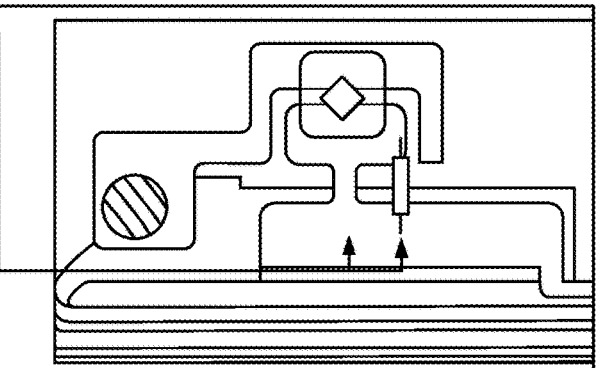

| $R_{sensor}$ | Tag | Phone Readout |
|---|---|---|
| 10 Ohm | Unreadable | Scan a tag... |
| 1 kOhm | Readable | tag detected! |

Turn-off ↓ / Turn-on ↑

FIG. 4B

CHEMICAL AND PHYSICAL SENSING WITH A READER AND RFID TAGS

CLAIM OF PRIORITY

This application is a continuation of U.S. application Ser. No. 15/426,027, filed Feb. 6, 2017, now U.S. Pat. No. 10,157,340, which is a continuation of U.S. application Ser. No. 14/528,856, filed Oct. 30, 3014, now U.S. Pat. No. 9,563,833, which claims the benefit of prior U.S. Provisional Application No. 61/897,613 filed on Oct. 30, 2013, each of which is incorporated by reference in its entirety.

FEDERALLY SPONSORED RESEARCH OR DEVELOPMENT

This invention was made with government support under Contract No. W911NF-07-D-0004 and W911NF-13-D-0001 awarded by the Army Research Office. The government has certain rights in the invention.

TECHNICAL FIELD

The invention relates to sensors and methods of sensing.

BACKGROUND

Development of portable and low-cost technologies for chemical and physical sensing is important. Traditional solutions suffer from limitations, such as being expensive, bulky, or fragile, or requiring of trained personnel to operate. In addition, many traditional methods of sensing require physical contact of the device with the sensing element/material via wires or solid-state circuitry to acquire data.

SUMMARY

In one aspect, a method of detecting a stimulus can include detecting a output from a radio frequency identification tag including a sensor portion, the sensor portion configured to change resistivity when the stimulus can contact or interact with the radio frequency identification tag, whereby the resistivity change can alter the output of the radio frequency identification tag. The sensor portion can be configured to activate a circuit or deactivate the circuit, or change a detectable property of the circuit when contacted or having interacted with the stimulus.

The reader can be a device that that interprets output information in the radio frequency regime, for example, frequency, frequency shift, signal intensity, or other detectable information.

In certain embodiments, the method can include detecting the output of the radio frequency identification by a reader. The reader can include a hand held, mobile platform or stationary reader, which can include a smartphone, wifi access point, or similar device.

In certain embodiments, the stimulus can include an analyte. The stimulus can include a vapor. The stimulus can include a mold. The stimulus can include ethylene. The stimulus can include an alkene, an alkyne, an acid, a ketone, an ester, an aldehyde, an alcohol, an ether, a thiol, ammonia, mono-nitrogen oxide, or an amine. The stimulus can include thermal energy. The stimulus can include harmful ionizing radiation. The stimulus can include UV light. In circumstances where the stimulus is energy (e.g., thermal, radiation or light), the stimulus interacts with the tag.

In certain embodiments, the method can include producing a readable signal in a reader as a result of the resistivity change. The method can include turning off a readable signal in a reader as a result of the resistivity change.

In certain embodiments, the output can be detectable by a hand held reader after the frequency is shifted by detection of the stimulus. The output can be detectable by a reader after the output going through a physical object.

In certain embodiments, the stimulus can contact or interact with a portion of the surface of the radio frequency identification tag. The sensor portion can be located on a portion of a surface of the radio frequency identification tag. The sensor portion can be surrounded by an antenna coil. The sensor portion can include multiple sensing locations. The sensor portion can have a surface area less than the surface area of the radio frequency identification tag.

In certain embodiments, the radio frequency identification tag does not have to require a power source. The radio frequency identification tag can include one or multiple carbon nanotubes. The method can include altering an electrical connection within the radio frequency identification tag.

In another aspect, a tag for detecting a stimulus can include a radio frequency identification tag that includes a sensor portion, the sensor portion configured to change resistivity when the radio frequency identification tag can contact or interact with the stimulus, whereby the resistivity change alters a output of the radio frequency identification tag, wherein the sensor portion can include a circuit, and wherein the sensor portion can be configured to close the circuit or open the circuit when contacted with or having interacted with the stimulus.

In certain embodiments, the sensor portion can include a sensing material comprising a metal, an organic material, a dielectric material, a semiconductor material, a polymeric material, a biological material, a nanowire, a nanoparticle, a semiconducting nanoparticle, a carbon nanotube, a nanofiber, a carbon fiber, a carbon particle, carbon paste, or conducting ink, or combination thereof. In each instance, the sensing material can include a plurality of particles, each of which can be a nano-structured material.

In certain embodiments, the tag can be incorporated into a badge capable of being worn by a person.

In another aspect, a system for detecting a stimulus can include a radio frequency identification tag including a sensor portion, the sensor portion configured to change resistivity when the radio frequency identification tag can contact or interact with the stimulus, whereby the resistivity change can alter an output of the radio frequency identification tag, and a detector detecting the output from the radio frequency identification tag.

In certain embodiments, the detector can be a reader. The reader can be a hand held frequency reader, which can be a smartphone. The detector can become readable from unreadable after the resistivity change. The detector can become unreadable from readable after the resistivity change.

In certain embodiments, the system can include a dosimeter. The dosimeter can be a radiation dosimeter, a chemical warfare agent dosimeter, a sulfur dosimeter, or an ozone dosimeter. The system can monitor a pollutant or a chemical relevant to occupational safety.

In certain embodiments, the system can include a plurality of tags. Each of the plurality of tags can be capable of detecting at least one stimulus.

Other aspects, embodiments, and features will be apparent from the following description, the drawings, and the claims.

BRIEF DESCRIPTION OF THE DRAWINGS

FIG. 4A depicts the principle of Sensing Method 1; FIG. 4B depicts the principle of Sensing Method 2.

FIG. 12 shows turn-on sensing in response to exposure to (II) $NO_x$ and (IV) Clorox vapors.

DETAILED DESCRIPTION

Figure 1:
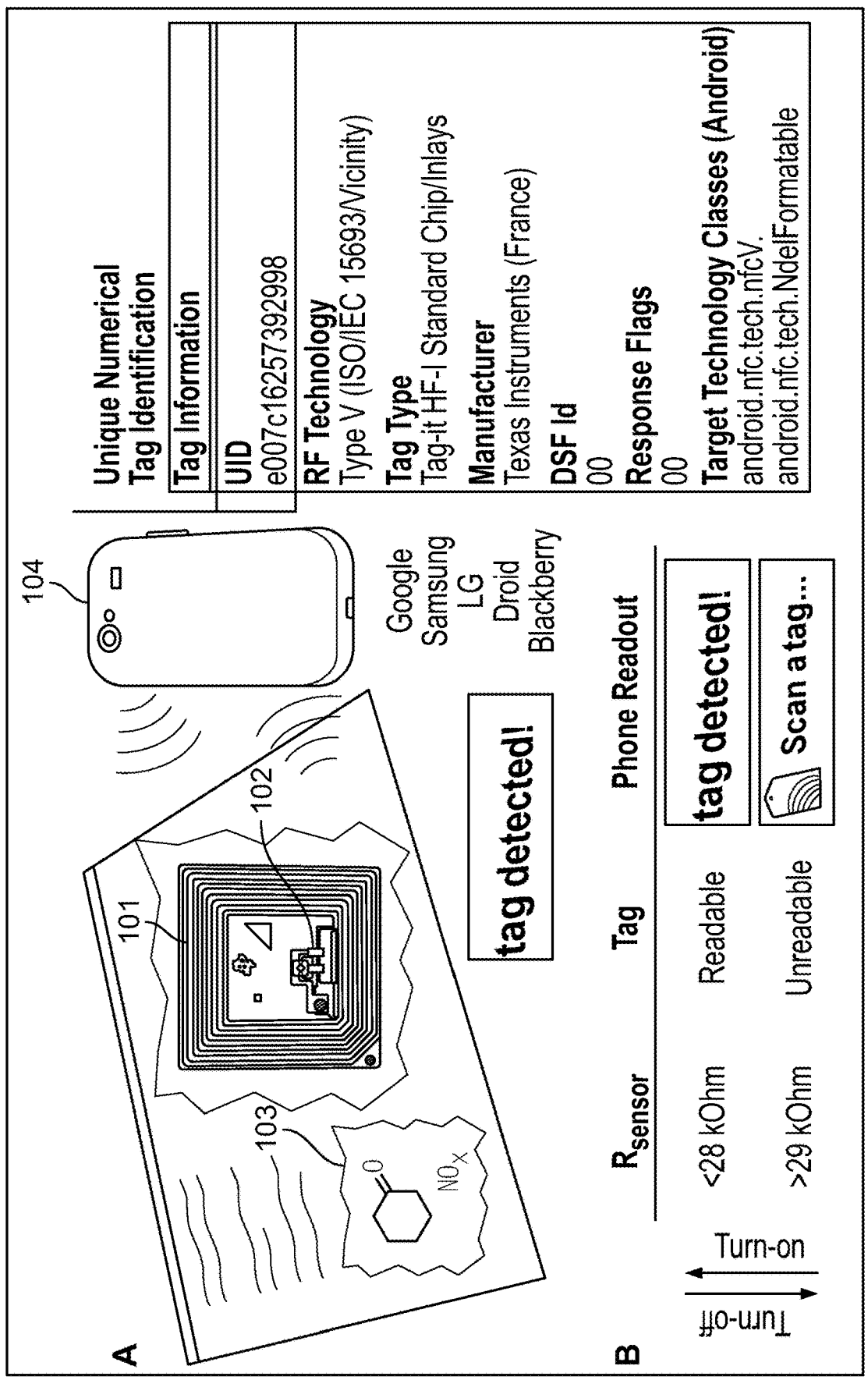
FIG. 1 shows the transmission of radio waves between a RFID tag and a smartphone.

Development of portable and low-cost technologies for chemical and physical sensing is important for human health, safety, and quality of life. Such systems can be used for point-of-care diagnosis of disease, detection of explosives and chemical warfare agents, prevention of spoilage of food and increasing efficiency in agriculture, analysis of oil and gas, detection of petrochemical leaks and spills, monitoring of environmental pollution, detection of radiation, and monitoring of temperature or heat energy exposure. Traditional improvements in this area increase performance through modification or re-engineering of existing platforms. Such strategies may include miniaturizing components to increase portability (e.g., portable gas chromatograph or mass spectrometer) or reducing cost (e.g., increasing the efficiency of the manufacturing). While these solutions may improve existing platforms in terms of portability, they still suffer from limitations, such as being expensive, bulky, or fragile, or requiring of trained personnel to operate. Furthermore, many traditional methods of chemical sensing require physical contact of the device with the sensing element/material via wires or solid-state circuitry to acquire data.

Examples of Some Sensors

The use of peroxide-based explosives has become increasing popular. Methods for determining a peroxide or a peroxide precursor can include forming a fluid mixture comprising a peroxide-reactive material, a light-emitting material, a support material or support material precursor, and, optionally, a catalyst, to produce a composition that is emissive in the presence of a peroxide, wherein the composition has a boiling point of at least 300° C. or greater. Methods for determining a peroxide can include exposing a composition comprising peroxide-reactive material to a vapor suspected of containing a peroxide, wherein the peroxide, if present, causes the composition to generate a determinable signal, wherein the composition has a boiling point of at least 300° C. or greater, and determining the signal.

One method of detecting an analyte in a sample includes a carbon-carbon multiple bond moiety comprising exposing a detection region of a detector including a heteroaromatic compound having an extrudable group and capable of undergoing Diels-Alder reaction with the analyte including a carbon-carbon multiple bond moiety to the sample, and detecting color change of a reaction mixture comprising the heteroaromatic compound based on the presence of the analyte in the sample. This method provides alkene and alkyne detection, differentiation, and quantitation that addresses the growing need of transducing relevant information (only previously attainable from sophisticated methods such as GC-analysis) with the favorable low-cost and ease-of-use attributes ascribed to more basic technologies. Using this method, a device can indicate the presence of specific classes of alkenes or alkynes in the gas phase, and can determine the total exposure of the device to said alkenes or alkynes, based on a colorimetric readout. Because this device is selective for certain classes of alkenes and alkynes, it allows for differentiation of compounds of interest that contain certain alkene or alkyne functionality. This method can make use of the color change that accompanies the transformation of an s-tetrazine moiety to a pyrimidine moiety upon reaction with unsaturated carbon-carbon bonds. See, for example, Application No. PCT/US2014/033037, which is incorporated by reference in its entirety.

Another method of detecting a stimulus includes using a dosimeter, such as a thermal dosimeter, which can measure the amount of light emitted from a crystal in a detector when the crystal is heated. A dosimeter can use a triazole as described by Coulembier. See, for example, O. Coulembier et al., *Macromolecules*, 2006, 39, 5617-5628, which is incorporated by reference in its entirety.

Sensors Using a Digital Reader

Sensing platforms that have the characteristics of being simple, inexpensive, yet sensitive and quantitative can be created. One approach to the area of chemical and physical sensing can be the development of sensing materials and devices that have the characteristics of being modular (i.e., easily modified for specific applications), wirelessly readable, and easily used and interpreted by individuals with no prior technical training.

Whitesides and co-workers have demonstrated chemical detection of analytes in biologically-relevant samples using smartphones. See, for example, Martinez, A. W. et al., *Anal. Chem.*, 2008, 80, 3699-3707, which is incorporated by reference in its entirety. These methods involve capturing an image of a colorimetric assay using an in-phone camera and analyzing it to correlate changes in color of a dye with the presence of biologically relevant analyte. This method, however, requires line-of-sight measurement that can be affected by potential artifacts arising from lighting conditions, positional angle, or hand-movement during image acquisition.

Potyraillo et al. and others demonstrated electronic wireless detection of chemical analytes using RFID technology. See, for example, Potyrailo, R. A. et al., *Anal. Chem.* 2006, 79, 45-51, which is incorporated by reference in its entirety. While this technology has the capability to perform non-line-of sight measurements that overcome some of the limitations of the colorimetric assays, they have limited portability as they require the use of advanced electronics devices, such as inductively coupled network analyzers or impedance spectrometers.

Studies have exploited custom-made, as well as commercially available RFID tags to monitor freshness of milk, freshness of fish, and growth of bacteria. See, for example, Tao, H. et al., *Adv. Mater.* 2012, 24, 1067-72; Potyrailo, R. A. et al., Battery-free Radio Frequency Identification (RFID) Sensors for Food Quality and Safety, 2012, each of which is incorporated by reference in its entirety. These studies relied primarily on correlating the changes in dielectric environment of the RFID tags (i.e., changes in C) with changes in the resonant frequency or resonant impedance of the LCR circuit. However, they are limited by a lack of selectivity toward chemical analytes and physical stimuli, and by the requirement for expensive radio frequency analysis equipment such as impedance and network analyzers for chemical detection.

Although RF technology has been recently applied towards wireless chemical sensing, current approaches have several limitations including lack of specificity to selected chemical analytes, requirements for expensive, bulky, fragile, and operationally complex impedance and network analyzers, and reliance on extensive data processing and analysis. See, Potyrailo R A, Surman C, Nagraj N, Burns A (2011) Materials and transducers toward selective wireless gas sensing. *Chem Rev* 111:7315-7354, Lee H et al. (2011) Carbon-nanotube loaded antenna-based ammonia gas sensor. *Microw Theory Tech IEEE Trans* 59:2665-2673, Potyrailo R A et al. (2009) Development of radio-frequency identification sensors based on organic electronic sensing materials for selective detection of toxic vapors. *J Appl Phys* 106: 124902, Fiddes L K, Yan N (2013) RFID tags for wireless electrochemical detection of volatile chemicals. *Sensors Actuators B Chem* 186:817-823, Fiddes L K, Chang J, Yan N (2014) Electrochemical detection of biogenic amines during food spoilage using an integrated sensing RFID tag. *Sensors Actuators B Chem* 202:1298-1304, Occhiuzzi C, Rida a., Marrocco G, Tentzeris M M (2011) Passive ammonia sensor: RFID tag integrating carbon nanotubes. 2011 *IEEE Int Symp Antennas Propag:* 1413-1416, each of which is incorporated by reference in its entirety.

Disclosed herein are a method and a system of converting inexpensive commercial NFC tags into chemical sensors that detect and discriminate analytes at part-per-thousand and part-per-million concentrations. This effort merges rational design of conductive nanostructured materials for selective chemical sensing with portable and widely distributed NFC technology to deliver a new method of acquiring chemical information about an NFC tag's local environment.

A commercially available technology-Near Field Communication (NFC)— can be used for wireless, non-line-of-sight chemical sensing. Many modern smartphones and similar devices (tablet computers, video game controllers, and smartphone accessories) can be equipped with NFC readers operating at peak frequency of 13.56 MHz. These readers can be tuned to interact with many types of commercially available wireless "tags"-simple electrical circuits comprising an inductor (L), a capacitor (C), and an integrated circuit (resistor (R)) supported on the surface of a substrate, such as a polymeric sheet. The phone can achieve communication by powering the tag via electromagnetic induction at the specified frequency and then receiving reflected attenuated signal back from the tag. See, for example, Curty, J. P. et al., *Springer*, New York, 2007, pp. 49-73, which is incorporated by reference in its entirety. This technology can be used in controlling access to facilities, ticketing of events, prevention of theft, and management of inventory. This technology can be applied to chemical sensing by introducing chemiresistive materials into the circuitry of the tag. Exposure of the modified tag to chemical vapors can alter the resistance of the sensing materials, and thus the resonant frequency of the modified tag, such that it becomes readable or unreadable when probed by a smartphone reader. With this method, vapors of nitric acid, ammonium hydroxide and cyclohexanone, can be detected. This technology can be extended to physical sensors as well, such as applications in temperature, heat energy exposure or radiation sensing.

Commercially available RFID tags can be combined with a digital reader, such as a hand held frequency reader, for example a consumer electronic smartphone, resulting in a fully integrated chemical and physical sensing platform. The sensing platform can be available to anyone, including those without a technical background. This platform has advantages over existing methods of chemical and physical sensing. For example, the sensing method can be non-line-of-sight (high frequency radio waves), and can receive information from the sensor tag through solid objects such as packages, walls, wood, and other non-metallic objects. The sensing tag does not require a power source, as it receives its power from the incoming radio waves. The data-acquiring device can be any commercially available smartphone equipped with near field communication (NFC) reader capabilities, including but not limited to Samsung, LG, Google, Blackberry, etc. manufacturers. The method is simple: no technical knowledge is required to perform a measurement.

Some differences between previous studies and this method include: i) The chemical detection is achieved using NFC technology instead of impedance spectroscopy; ii) The detector is a highly portable device such as a. Smartphone, instead of a very bulky complex instrument (e.g., a network analyzer). Besides portability, the smartphone has additional utility in chemical detection because the information obtained from the chemical sensor can be coupled with other sensors within the smartphone (e.g., GPS, email) for automated identification of position and communication of information. iii) Ability for wireless chemical sensing over distance of 5 cm of solid material was demonstrated, as opposed to through a distance of a single paper sheet. iv) This method incorporates chemiresistors into the existing circuitry of a tag by drawing as opposed to depositing sensing materials on top of the antenna. v) This method requires no data workup for signal processing, while existing methods often require substantial amount of data processing for interpreting information. vi) This method does not require additional equipment for reading the magnetic memory. vii) This method relies on changes on resistance of a selective chemiresistive or physiresistive material for chemical sensing, while existing methods rely on non-specific changes in capacitance. viii) This method relies on molecular recognition for selectivity, and does not require principal component analysis, and so on.

Figure 18:
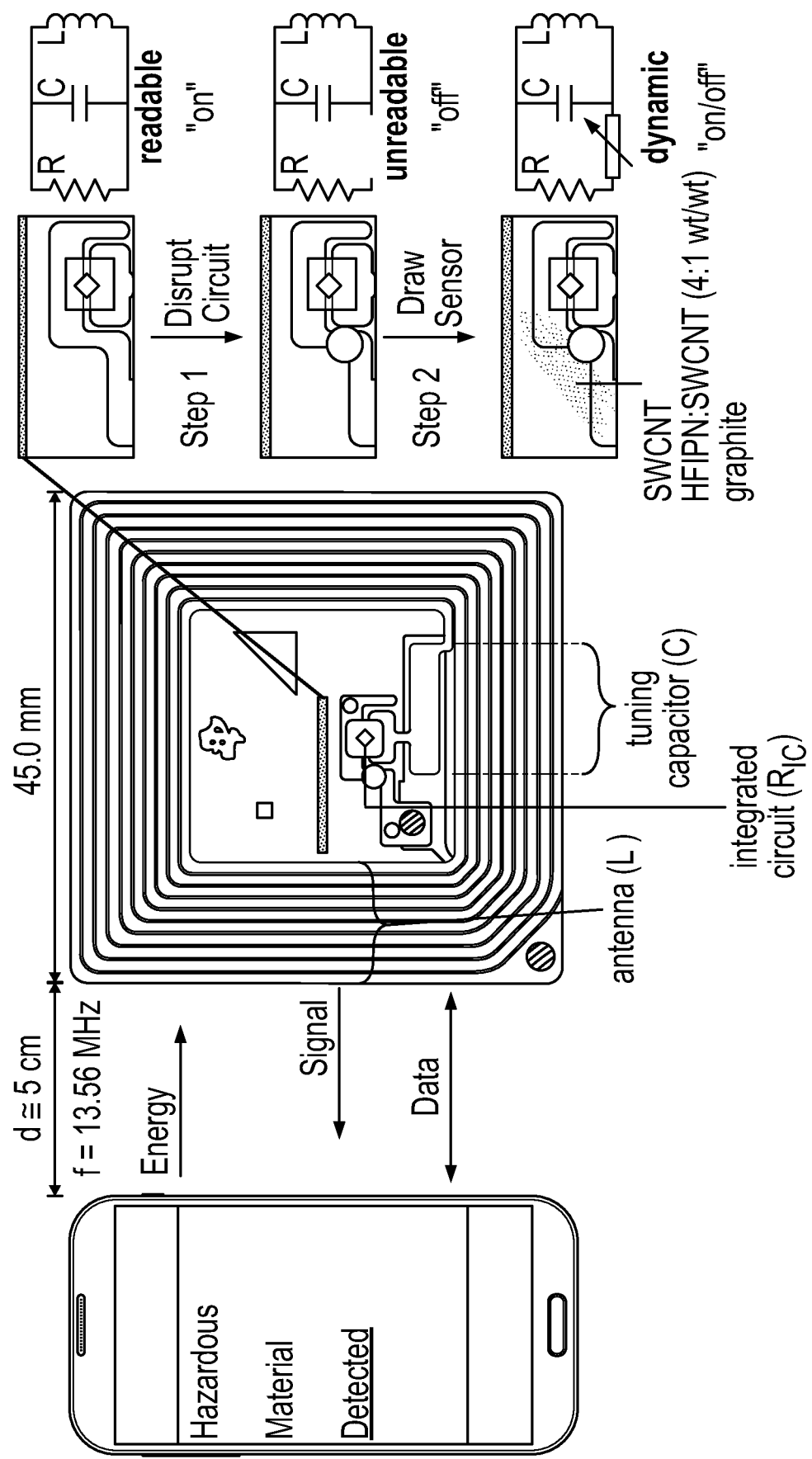
FIG. 18 shows conversion of an NFC tag into a CARD enables wireless RF detection of chemical analytes with a smartphone.

FIG. 18 shows the adaptation of a nascent technology embedded in modern smartphones-Near Field Communication (NFC)—for wireless electronic, portable, non-line-of-sight selective detection of gas-phase chemicals. NFC-enabled smartphones communicate with NFC tags by simultaneously energizing the NFC tag with an alternating magnetic field (f=13.56 MHz) through inductive coupling and transferring data by signal modulation. NFC tags are converted into Chemically Actuated Resonant Devices (CARDs) by disrupting the LCR circuit (Step 1) and recompleting the circuit with a stimuli-responsive variable circuit component by drawing (Step 2) with solid sensing materials.

This concept can be demonstrated by (i) incorporating carbon-based chemiresponsive materials into the electronic circuitry of commercial NFC tags by mechanical drawing, and (ii) using an NFC-enabled smartphone to relay information regarding the chemical environment (e.g., presence or absence of a chemical) surrounding the NFC tag. In this way, part-per-million (ppm) concentrations of ammonia and cyclohexanone and part-per-thousand (ppth) concentrations of hydrogen peroxide can be detected and differentiated. Wireless acquisition and transduction of chemical information can be coupled with existing smartphone functions (e.g., GPS).

Many commercial smartphones and mobile devices are equipped with NFC hardware configured to communicate wirelessly with NFC "tags"—simple electrical resonant circuits comprising inductive (L), capacitive (C), and resistive (R) elements on a plastic substrate (FIG. 18). The smartphone, such as the Samsung Galaxy S4 (SGS4), employed in this study, communicates with the battery-free tag by powering its integrated circuit (IC) via inductive coupling at 13.56 MHz. See, Nitkin P V., Rao K V S, Lazar S (2007) An overview of near field UHF RFID. 2007 *IEEE Int Conf RFID:*167-174, which is incorporated by reference in its entirety. Power transferred from the smartphone to the IC is, among other variables, a function of the transmission frequency (f), the resonant frequency ($f_0$), the quality factor (Q), and the circuit efficiency ($\eta$), which in turn are functions of L (H), C (F), and R ($\Omega$) of the smartphone and NFC resonant circuit components. See, Jing H C, Wang Y E (2008) Capacity performance of an inductively coupled near field communication system. 2008 *IEEE Antennas Propag Soc Int Symp* 2:1-4, which is incorporated by reference in its entirety. Integration of chemiresponsive materials into commercial NFC tags produces stimuli-responsive variable circuit components that affect power transfer between the tag and a smartphone in the presence or absence of chemical stimuli. The resulting programmable Chemically Actuated Resonant Devices (CARDs) enable non-line-of-sight smartphone chemical sensing by disrupting or allowing RF communication.

In one method, commercially available high frequency (HF) radio frequency identification tags compatible with a reader can be converted into chemical and physical sensors. The reader can be a digital reader, which can be a handheld frequency reader. The reader can be portable. The reader can be a smartphone. In parallel with the sensing capability, a smartphone reader can read other things, such as GPS coordinates, acceleration, light intensity, altitude, etc. Coupling these capabilities in one portable reader can have unprecedented utility.

This technology can be extended to temperature, heat energy exposure and radiation sensing as well. The modification of the tag can involve integration of chemiresistive sensing materials by drawing or dropcasting onto the surface of the tag. Depending on the design, the tag can become readable or unreadable when exposed to vapors of chemicals or physical stimulus.

A stimulus can include an analyte. The stimulus can include a vapor, a gas, a liquid, a solid, a temperature change, heat energy exposure and so on. The stimulus can include an ethylene, a mold, an acid, a ketone, a thiol, an amine, and so on. Using RFID, a stimulus can be detected; for example, vapors of nitric acid and cyclohexanone can be detected; and ethylene and mold can be detected; and biological warfare agents can be detected. Cumulative exposure of analytes can be detected and quantified with a dosimeter.

A stimulus can include a physical stimulus. The physical stimulus can include light, heat, or radiation. Using RFID, a stimulus can be detected for example, exposure of a tag to heat can be detected; and radiation and light can be detected. Cumulative exposure of physical stimulus can be detected and quantified with an RFID dosimeter.

A sensing material can produce detectable change in resistance and/or capacitance upon chemical, biological, or physical changes around the sensing device. A property of a sensing material that can change upon exposure to the environment includes, but is not limited to, change in capacitance, change in resistance, change in thickness, change in viscoelasticity, or a combination thereof.

A sensing material can include a metal, an organic material, a dielectric material, a semiconductor material, a polymeric material, a biological material, a nanowire, a semiconducting nanoparticle, a carbon nanotube, a carbon nanotube network, a nanofiber, a carbon fiber, a carbon particle, carbon paste, or conducting ink, or combination thereof.

Different approaches can be taken to introduce chemical and physical sensing materials. For example, sensing materials can be introduced into two different locations within a commercial RFID tags. Sensing materials include variable resistors that alter their resistance in response to a stimulus. A stimulus can be a chemical stimulus, a physical stimulus, a biological stimulus, etc. The detection of a stimulus can be achieved by switching the tag between a "readable" and "not readable" state, by exposure to a stimulus, such as chemical vapors or changes in temperature or heat energy exposure, for example.

Figure 19:
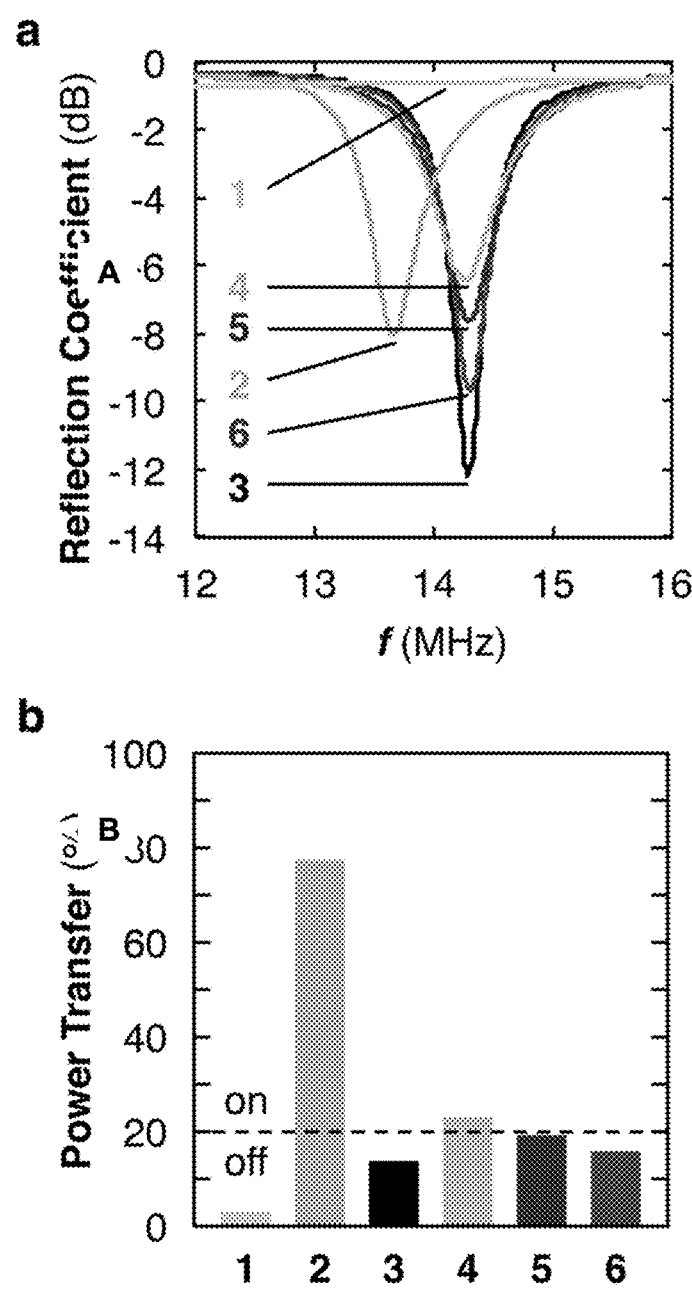
FIG. 19 shows the presence of an analyte influences the power transfer between the smartphone and CARD. Graph A shows average (n=5) reflection coefficient ($S_{11}$) of (1) baseline (no tag present), (2) unmodified NFC tag, (3) circuit-disrupted tag, (4) CARD-2, (5) CARD-2 in the presence of cyclohexanone (equilibrium vapor pressure at ambient temperature and pressure) for 5 s, and (6) for 1 min. Graph B shows average (n=5) estimated power transfer ($P_t$) (13.53 MHz-13.58 MHz) from SGS4 to CARDs described in 1-6.

When a stimulus contacts or interacts with a sensor, the resistivity can change. The contact or interaction can produce a readable signal in a hand held frequency reader as a result of the resistivity change. Alternatively, the contact or interaction can turn off a readable signal in a hand held frequency reader as a result of the resistivity change. Output can be detected after the output is shifted by detection of the stimulus. Even after going through a physical object, the output can still be detected. Detecting the stimulus is not limited to the frequency output, but can include, but is not limited to, a change in frequency, a change in q factor, a change in bandwidth, and a combination of these. These changes can result in increasing or decreasing the power transferred between the reader and radio frequency identification tag. Increasing or decreasing the power transferred between the reader and radio frequency identification tag can result in a change of the readout of the tag. For example, FIG. 19 shows the estimated power transfer between the phone and CARDs, as it relates to the readability of those CARDs and FIG. 26 exemplifies how this information was obtained and processed.

In one approach, a specific electric connection within an RFID tag can be disrupted, for example by cutting, and this connection can be reestablished by deposition of a chemiresistive sensing material by either drawing or dropcasting. An RFID tag can include an integrated circuit (IC) containing magnetic memory material where the tag identification is stored. Depending on the sensing material and the stimulus, the tag can become readable and is classified as a "turn ON sensor," or become unreadable and is classified as a "turn OFF sensor".

In one method, the tag is not readable by a reader when no stimulus is present, because the resistance of the sensor is too high. When the tag is placed in the presence of a stimulus that causes the sensor to change its resistance, the tag can become readable once the resistance value crosses a threshold value. This is a turn-on sensing method.

In another method, the tag can be readable by a reader when no analyte is present, because the resistance of the sensor is high enough to allow current to flow through the integrated circuit. When the tag is placed in the presence of a stimulus that causes the sensor to change its resistance, the tag can become unreadable once the resistance value drops below a certain threshold value. This is a turn-off sensing method.

In another method, instead of a turn-on sensing or a turn-off sensing, a series of data can be collected, which can provide a quantitative analysis of a stimulus.

In another method, parallel integration can be used to integrate a sensing material into a portion of the tag containing the integrated circuit by drawing or dropcasting. This approach can "turn ON" or "turn OFF" detection of a stimulus, and can be complimentary to the first approach because requirements for resistance of the deposited sensing material can be different (which may have an effect on the dynamic range and the detection limit of chemical sensors towards different analytes).

A radio frequency identification tag does not have to require a power source. RFID tags can be either passive, active or battery-assisted passive. An active tag has an on-board battery and periodically transmits its signal. A battery-assisted passive has a small battery on board and is activated when in the presence of a RFID reader. A passive tag has no battery.

When detecting a stimulus comprising detecting an output from a radio frequency identification tag including a sensor portion, the stimulus does not have to contact or interact with the entire surface of the tag. The sensor portion has a surface area less than the surface area of the radio frequency identification tag. The sensor portion can be located on a portion of a surface of the radio frequency identification tag, and the stimulus can contact a portion of the surface of the radio frequency identification tag. In addition, the sensor portion can have multiple sensing locations, and a single tag can be used to detect more than one stimulus.

A system for detecting a stimulus comprising a radio frequency identification tag can include a sensor portion, the sensor portion configured to change resistivity when the radio frequency identification tag contacts or interacts with the stimulus, whereby the resistivity change alters an output of the radio frequency identification tag, and a detector detecting the output from the radio frequency identification tag. The detector can include a reader. The reader can include a hand held frequency reader. A method of detecting a stimulus can include detecting an output from a radio frequency identification tag including a sensor portion.

The system can include a real time sensor. The system can include a dosimeter, such as a radiation dosimeter, a chemical warfare agent dosimeter, or an analyte dosimeter, such as, for example, an ethylene dosimeter, a sulfur dosimeter, or an ozone dosimeter. The system can be used to monitor pollutants or chemicals relevant to occupational safety. Pollutants or chemicals can include fumes from automotive/equipment exhaust, volatiles from manufacturing, painting, or cleaning, or vapors in underground mines.

A sensor can include an electronic circuit comprising electronic components. Electronic components can include resistors, transistors, capacitors, inductors and diodes, connected by conductive wires or traces through which electric current can flow. The electrical connection within the radio frequency identification tag can be altered. The resistivity of the sensor can change when the sensor is exposed to a stimulus. Contacting or interacting with a stimulus can close the circuit or open the circuit, or otherwise alter the properties of the circuit.

A sensor can include a sensing material such as a metal, an organic material, a dielectric material, a semiconductor material, a polymeric material, a biological material, a nanowire, a semiconducting nanoparticle, a carbon nanotube, a nanofiber, a carbon fiber, a carbon particle, carbon paste, or conducting ink, or combination thereof. A sensing material can include organic electronics materials, doped conjugated polymers, or inorganic materials. A sensing material can include biological molecule receptors, living cells, antibodies, aptamers, nucleic acids, functionalized biological molecules, and so on.

A tag for detecting a stimulus comprising a radio frequency identification tag can include a sensor portion, the sensor portion configured to change resistivity when the radio frequency identification tag contacts or interacts with the stimulus, whereby the resistivity change alters an output of the radio frequency identification tag, wherein the sensor portion includes a circuit, and wherein the sensor portion is configured to close the circuit or open the circuit when contacted ir having interacted with the stimulus. The tag can be worn as a badge for occupational health and safety personnel, military personnel, etc., detecting a hazardous analyte or radiation.

A tag can include a substrate material. The substrate can include paper, plastic, a polymer, a metal, a metal oxide, a dielectric material, wood, leaves, skin, tissue, and so on. The substrate can include a metal oxide material. The substrate can be flexible; the substrate can be flat. The tag can also be embedded inside other objects (e.g., inside a capsule or a wall) or inside living systems (e.g., implanted inside a body).

A tag can include an antenna, providing a link between a frequency reader and a tag, receiving and transmitting a signal, and serving as a conduit that moves data back and forth. The antenna can include coils surrounding a sensor; the antenna can include a dipole antenna. A tag can include an antenna group including a plurality of antennas or an antenna array.

The ability to easily detect the existence of an analyte on a base signal using an ON/OFF binary detection method is of increasing interest in today's society. A system using a portable reader, such as a smartphone, enables everyone to determine the status of certain analytes anywhere without complicated analysis of a signal. When the amount of an analyte changes, a handheld frequency reader can turn on or turn off a signal, sending a notification of the presence or absence of the analyte. Another advantage of using a smartphone is that it carries within it many additional capabilities that can be coupled with chemical sensing to increase utility. For instance, a smartphone reader can identify a chemical spill and immediately send an emergency text or email alert identifying position of a spill using GPS. Another example could be wireless networks that monitor spatiotemporal changes in concentrations of chemical emissions and send emergency alerts when safe thresholds are exceeded. Coupling of such capabilities can enable unprecedented utility of chemical sensors in everyday life.

A tag can serve as a binary logic element providing either a "1" or a "0" as pre-defined by functional sensor material, which offers advantages in terms of simplicity of implementation and does not require any sophistication by the end user. If viewed as a binary logic element, the tag could be used in further elaborations of that logic. For instance, a unique combination of the readout of multiple tags could be assigned to a specific meaning. For example, if three separate tags are "coded" for three separate analytes by virtue of the sensor materials used to make them, then $2_{43}$ possible combinations exist, which could each mean something unique and significant. For example, if those analytes were food related, then one could possibly determine which type of food the sensors are attached to based on a combination of tag read-out, within a certain probability. Another example would be three tags that are "coded" with the same sensor material that has been designed to react at different concentrations of analyte. The combination of tag readout would allow one to determine, within some margin of error, the concentration of the analyte of interest.

Figure 21:
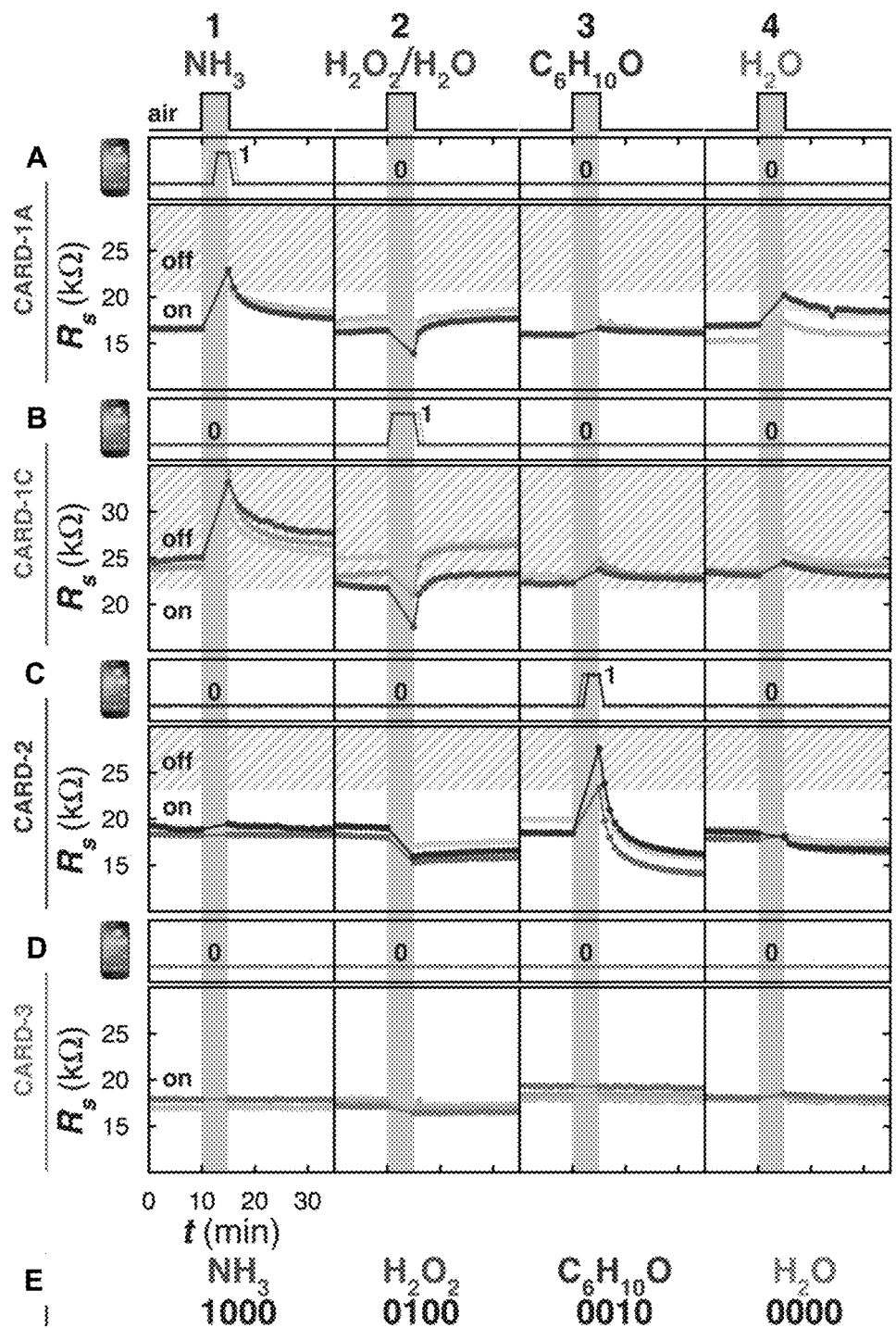
FIG. 21 shows arrays of CARDs enable identification and discrimination of analytes. Response of programmed (n=3) (A) CARD-1A; (B) CARD-1C; (C) CARD-2; and (D) CARD-3 to single 5 min exposures of (1) $NH_3$ (35 ppm), (2) $H_2O_2$ (225 ppm), (3) cyclohexanone (335 ppm), and (4) $H_2O$ (30,000 ppm) as monitored with a SGS4 (top) and multimeter (bottom). Shaded boundary indicates estimated $R_t$ for each respective CARD based on the traces shown. Compiled binary SGS4 responses (E), of CARD-1A, -1C, -2, and -3 codify the identity of the gases tested in this study.

The binary on/off readability of CARDs by the smartphone can be a powerful approach for converting analog physical inputs (presence or absence of a chemical vapor within a defined threshold) into a digitized output (1 and 0, respectively) that conveys meaningful information about the local chemical environment of the CARDs. The advantage of a binary-readout is that it is the simplest possible output representation of input information, and hence allows modular multiplexing of different CARD combinations. Taken together, the data presented in FIG. 21 suggest that discrimination and identification of multiple analytes can be achieved with a smartphone by converting the output of binary CARDs ("on"/"off") into multi-CARD logic (sequences of 0s and 1s) (FIG. 21 Graph E). This analytical approach has practical limitations in its implementation; however, it may be particularly useful in resource-constrained scenarios or high throughput applications where information about the presence or absence of specific chemicals at specified thresholds is critically important. Such applications may include detection of an acceptable threshold (e.g., permissible exposure limit for a chemical) that provides valuable actionable information in dynamic, complex environments (e.g., chemical release within a public space). Even under circumstances wherein the chemical of interest can be readily detected by the human nose, a differentiating feature of a smartphone-based sensing strategy over human-olfactory detection or visual inspection of a colorimetric test is the ability to efficiently bring sensed information into the information technology infrastructure.

An inexpensive, simple, rapid, and modular approach for converting commercially available NFC tags into chemically actuated devices can communicate with a smartphone via radio waves. This approach enables electronic wireless, non-line-of-sight detection and discrimination of gases and vapors at part-per-million and part-per-thousand concentrations. This technology provides binary ("on"/"off") information about the presence or absence of a chemical analyte regarding designated concentration thresholds, (e.g., NIOSH STEL) within the local environment of the sensor tag, and is capable of differentiating multiple concentrations of one analyte or multiple analytes using multi-tag logic. The general sensing strategy involving wireless communication between NFC tags and smartphones is modular and can be generalized to incorporate many types of chemiresponsive materials to enable selective detection of diverse chemical changes. Nevertheless, the significant challenges that remain to realize the full potential of this wireless sensing approach includes: (i) chemical and materials science innovations to improve the sensitivity and selectivity of chemiresponsive materials to chemical analytes; (ii) improving device-to-device performance reproducibility by advancing the state-of-the-art of nanostructured carbon deposition techniques and; (iii) enabling continuum measurement CARD readout capabilities. The combination of chemical sensing with other capabilities within the smartphone (e.g., GPS) may enable additional utility in applications involving tracking and tracing. As a result of the portability and increasingly ubiquitous use of smartphones and mobile devices, this platform can enable applications in personalized and widely distributed chemical sensing wherein the acquisition of chemical or physical information was previously unattainable.

EXAMPLES

Choice of Tags and Phone

Commercially available "dry" Texas Instruments HF-I Tag-It Plus Transponder Inlays (TI-Tag) can be used to demonstrate converting a commercially available tag into a chemical sensor. These tags were chosen based on their chemically insensitive substrate backing, access to transponder circuitry, and commercial availability. The unmodified tags are composed of a polyethylene terephthalate substrate (which also serves as a dielectric layer for the capacitor), an aluminum antenna serving as an inductor (L), a parallel-plate aluminum capacitor (C), and a silicon integrated circuit (IC) chip (R), all connected in parallel, forming an LCR resonant circuit.

Google Nexus S can be used as the primary NFC-enabled smartphone for this study, due to its wide circulation and the fact that it was the first smartphone to include both NFC hardware and software support. This phone is equipped with an RFID reader developed to operate within NFC standards. The RFID reader comprises a signal transmitting RFID controller and a signal receiving transponder. When used with unmodified TI-tags, the Nexus S has a read rage of 5 cm through solid, non-metallic objects such as paper, wood, and plastic.

Figure 2:
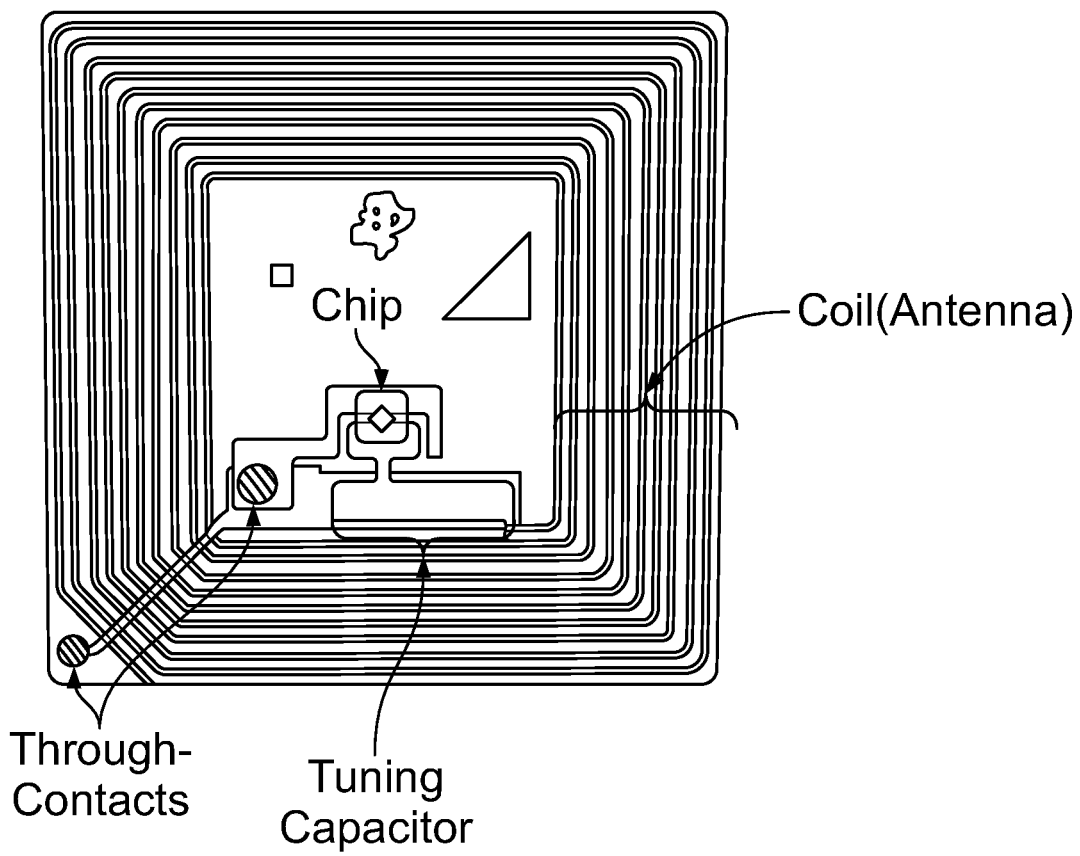
FIG. 2 shows a commercially available RFID tag.
Figure 3:
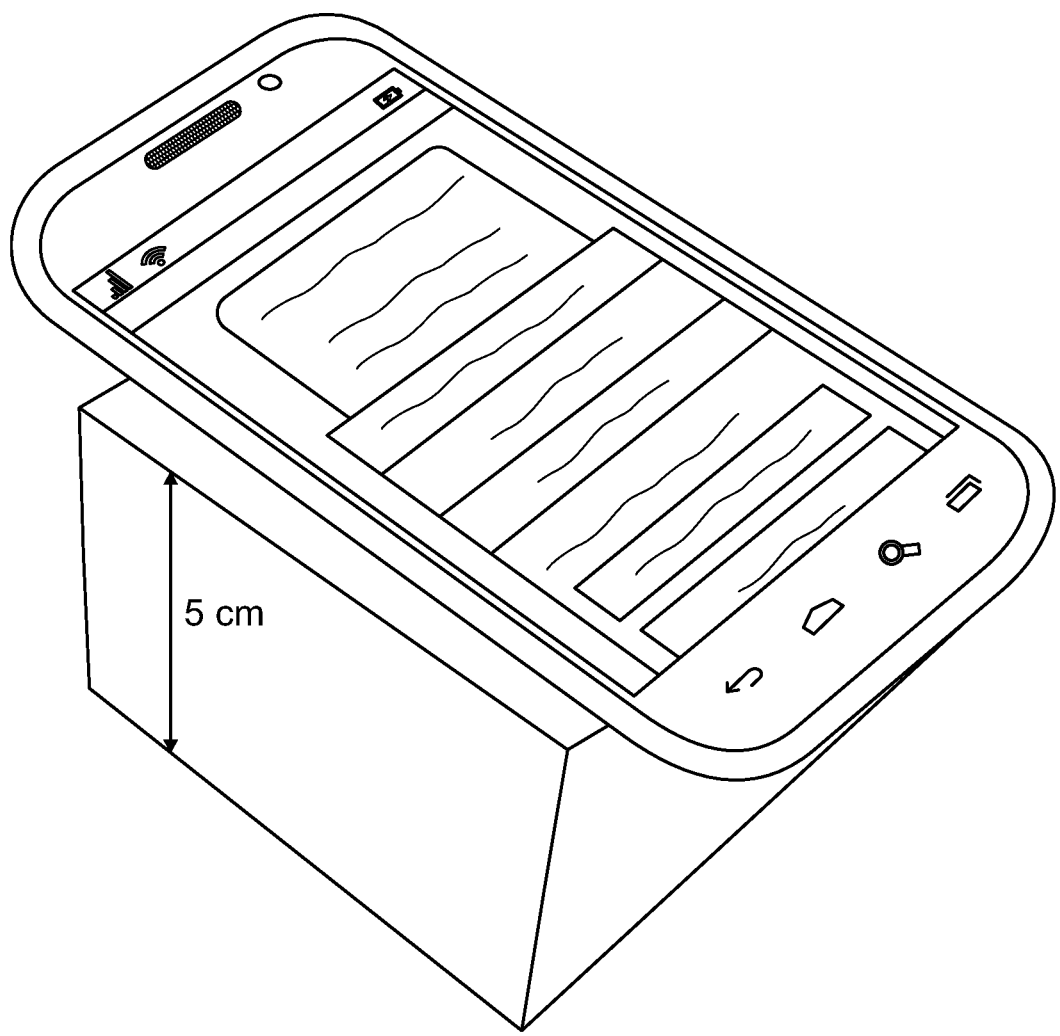
FIG. 3 demonstrates the readability of an RFID tag through a stack of Post-It notes with a thickness of 5 cm using Google Nexus S.

In FIG. 1, high frequency radio waves are transmitted to a modified RFID tag, which reflects radio waves back to the smartphone that carry with them information about the unique tag identification. Apps can be used; examples of Apps include NFC TagInfo from google play and NFC Reader from google play. FIG. 1 demonstrates the ability to link sensing response to a serial number. The transaction can happen in the cloud. Depending on the sensing mechanism, the modified RFID tag is either "readable" or "unreadable" by the smarthphone. The RFID tag can be interrogated through solid material, non-metallic material. FIG. 2 shows a commercially available RFID tag. FIG. 3 demonstrates the readability of an RFID tag through five Post-It notes (~5 cm). In addition to paper, a sensor can also read through other materials. The examples of other materials which a signal can penetrate include paper, wood, plastic, leather, skin, plastic composites, wood composites, slate, non-metallic objects, bark, leaves, the skin of fruit, clothing, cloth, textiles, water, organic liquids, brine, blood plasma, bodily liquids, concrete, drywall, glass fiber, non-metallic composite materials, and so on.

Instrumental Analysis

A vector network analyzer (VNA) was used to monitor the analog signal response of the modified TI-tags, the signals generated by the smartphone, and the modulation of signal that occurs upon collision of the smartphone-generated signal with the modified tag with and without analytes present. Analog resonant frequency data was acquired with an Agilent E5061B network analyzer by employing a custom-made loop antenna to monitor reflection across a frequency range of 10 MHz-20 MHz at 50Ω system impedance.

Conversion of Commercially Available RFID Tags into Chemical Sensors

The TI-tags can be converted into dynamic radio frequency sensor tags by inserting a chemiresistor in series with the IC, such that it is also in series with the capacitor and antenna. This modification is a two-step process. First, the TI-tag is rendered unreadable when probed by a conventional smartphone by disrupting one of the connections leading to the IC chip. Second, this connection is reestablished by drawing a chemiresistor in-between the capacitor and the IC lead.

Sensing Example

A system for detecting a stimulus can have a radio frequency identification tag 101 including a sensor portion 102, the sensor portion configured to change resistivity when the radio frequency identification tag contacts or interacts with the stimulus 103, whereby the resistivity change alters an output 104 of the radio frequency identification tag, and a detector 104 detecting the output from the radio frequency identification tag (FIG. 1).

In FIGS. 4A and 4B, a high frequency RFID tag is modified by cutting at the location between the capacitor and the integrated circuit. Sensing material was then deposited next to the location where the tag had been cut until the desired electrical resistance ($R_s$) was achieved. $R_s$ was determined using a multimeter. The initial resistance was recorded, and measured several times to ensure that it remained steady under ambient conditions. In the case of a turn-off sensing experiment, the tag readability by the smartphone was confirmed. In the case of a turn-on sensing experiment, the tag was unreadable by a smartphone.

The tag was then exposed to analyte of interest. $R_s$ was measured at multiple time points; upon each measurement, an attempt to interrogate the tag with the smartphone was made immediately after $R_s$ measurement, and the values and readability were recorded. Upon crossing a sensor threshold value, the tag became unreadable (turn-off sensor) or readable (turn-on sensor). The experimental procedure of measuring $R_s$ and interrogating the tag with a smartphone was continued after the threshold value was crossed. In the case of a reversible sensor, the above experimental procedure was repeated the desired number of times.

This method has advantages over other methods of chemical and physical sensing. The advantages include detection of cyclohexanone at low detection limits, RFID chemical sensing with a cell phone, direct integration of sensing material into mass-produced NFC inlay, quantitation of analyte with a smartphone, and so on.

FIG. 4A shows an enlargement of the chip and capacitor of FIG. 2, with a depiction the principle of Sensing Method 1. FIG. 4B shows an enlargement of the chip and capacitor of FIG. 2, with a depiction of the principle of Sensing Method 2.

Figure 5:
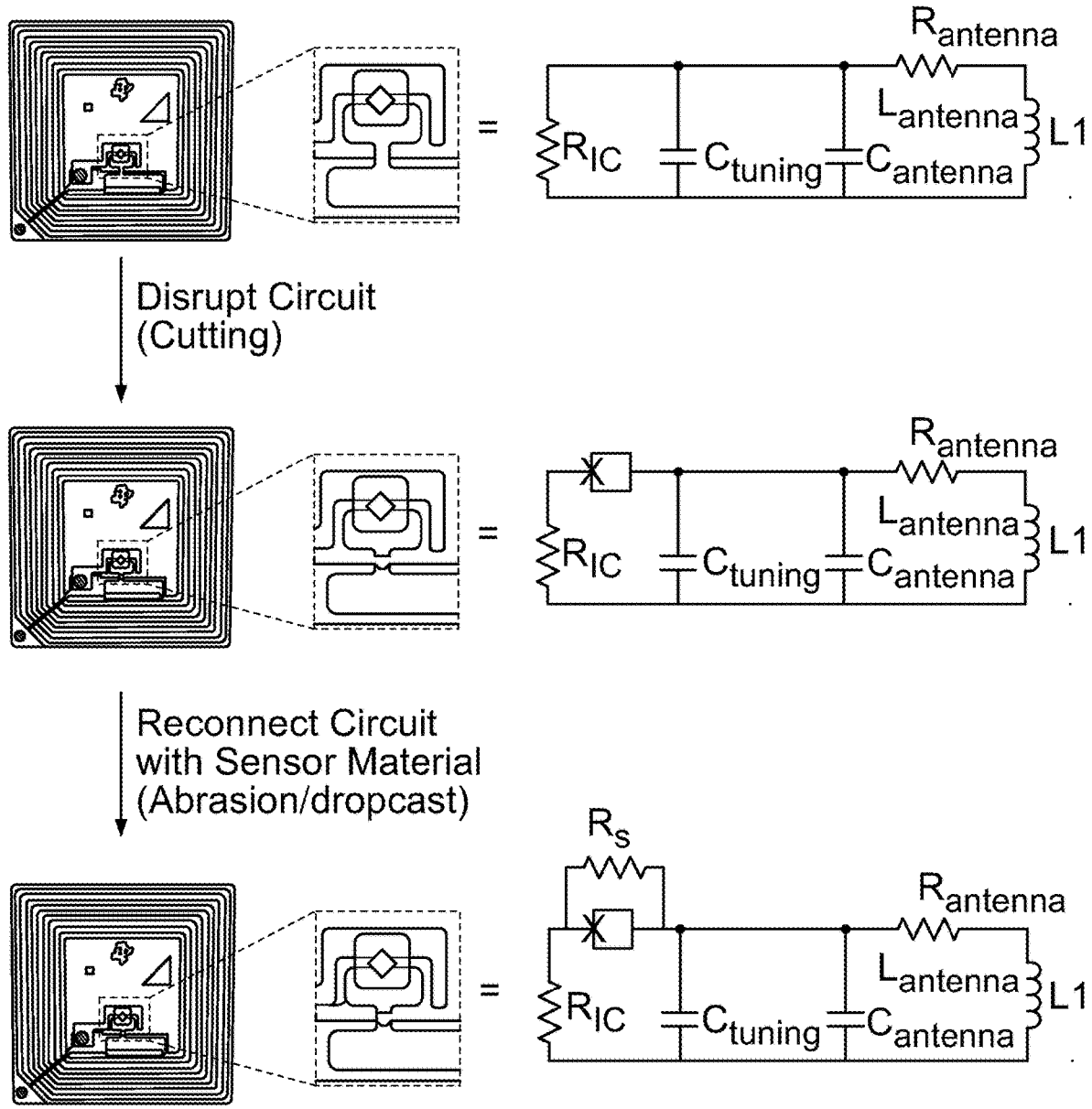
FIG. 5 shows graphical representations and equivalent electronic circuit diagrams of a modification process for Sensing Method 1.
Figure 6:
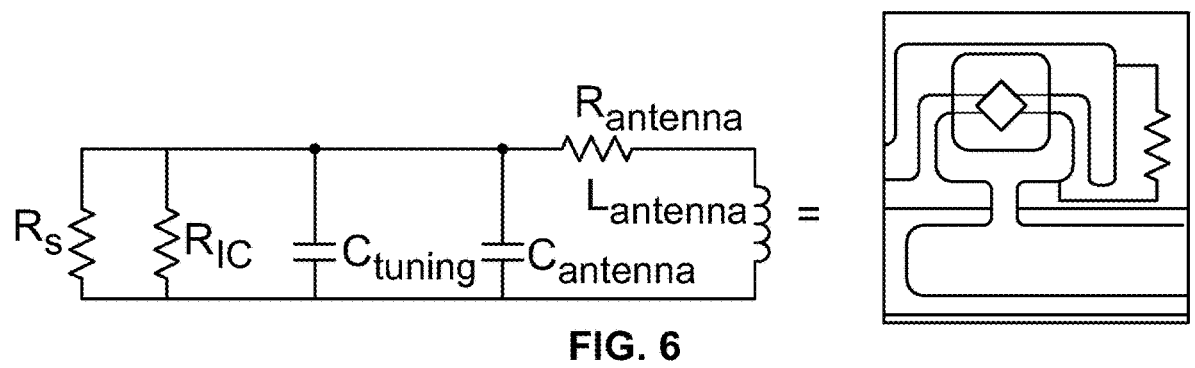
FIG. 6 shows a graphical representation and equivalent electronic circuit diagram of the result of the modification process for Sensing Method 2.

FIG. 5 shows graphical representations and equivalent electronic circuit diagrams of a modification process for Sensing Method 1 using a commercially available RFID tag (Texas Instruments Tag-It HF-1).

Figure 7A:
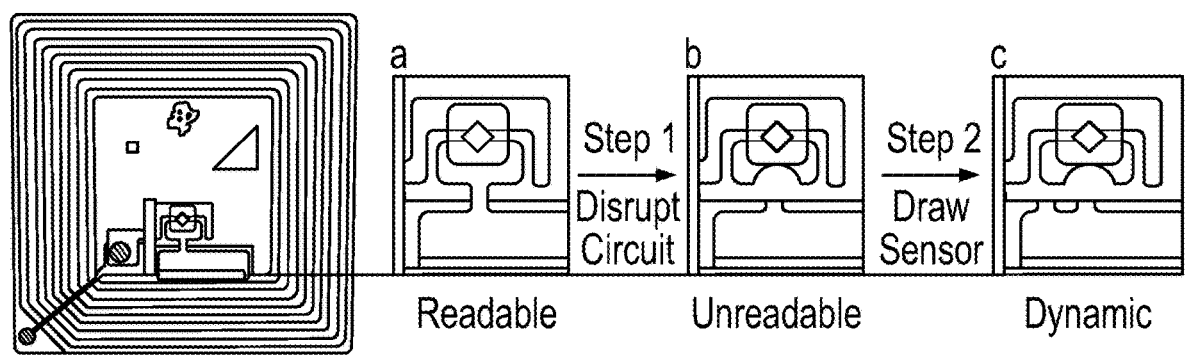
FIG. 7A shows two-step modification of tags with variable resistors.

A high frequency RFID tag can be modified by cutting at the location between the capacitor and the integrated circuit (FIGS. 7A and B). Sensing material was then deposited next to the location where the tag had been cut until the desired $R_s$ was achieved. $R_s$ was determined using a Fluke 114 true RMS multimeter. The initial resistance was recorded, and measured several times to ensure that it remained steady under ambient conditions. In the case of a turn-off sensing experiment, the tag readability by the smartphone was confirmed. In the case of a turn-on sensing experiment, the tag unreadability by a smartphone was confirmed.

The tag was then exposed to analyte of interest. $R_s$ was measured at multiple time points; upon each measurement, an attempt to interrogate the tag with the smartphone was made immediately after $R_s$ measurement, and the values and readability were recorded. Upon crossing a sensor threshold value, the tag became unreadable (turn-off sensor) or readable (turn-on sensor). The experimental procedure of measuring $R_s$ and interrogating the tag with a smartphone was continued after the threshold value was crossed. In the case of a reversible sensor, the above experimental procedure was repeated the desired number of times.

Integration of Chemiresistive Sensing Materials into RFID Tags Alters their Resonant Frequency.

A TI-tag can be viewed as a simple electrical circuit that consists of an inductor (L), a capacitor (C), and a resistor (R) connected in parallel. Equation 1 describes the resonant frequency, $f_0$ (Hz) of this type of circuit (LCR circuit) as a function of L, C, and R. The inductance in this circuit is a function of the geometry of the antenna, the capacitance is a function of the physical geometry of the conductors and the dielectric constant of the material between these conductive plates (i.e., the supporting polymeric substrate), and R is the effective resistance of all the circuit elements within the tag.

$$f_0 = \frac{1}{2\pi}\sqrt{\frac{1}{LC} - \left(\frac{R}{L}\right)^2} \tag{1}$$

The tags can be rendered chemically sensitive via a simple, two-step modification procedure, in which selective chemi- or physi-resistive sensor elements are incorporated into the LCR circuit (FIG. 7A). This method exploits the hypothesis that the resonant frequency of the RFID tag can be influenced by its chemical environment by altering R of the LCR circuit. The measured total resistance, R, of three different tags was measured with a multimeter by contacting the tag on either side of the sensor location and then compared to the resistance of the material located between the multimeter electrodes, $R_s$, by removing it from the tags and measuring its resistance independent of the tag. In the case of an unmodified tag, R=0.5Ω and $R_s$ 0.5Ω (FIG. 7A (a)). In the case of a tag wherein the conductive pathway between the capacitor and IC was absent, R 22.5 MΩ and $R_s \cong \infty$ (FIG. 7B (b)). In the case where a conductive pathway between the capacitor and IC was reestablished with a sensor, R 30 kΩ. and $R_s$=30 kΩ (FIG. 7A (c)). These experiments suggest that $R_{circuit}$=22.5 MΩ; therefore, the measured quantity R can be understood as behaving according to Ohm's law:

$$\frac{1}{R} = \frac{1}{R_s} + \frac{1}{R_{circuit}} \tag{2}$$

In the case of the sensors employed in this study, $R_s \ll R_{circuit}$ and therefore it can be assumed that $R \cong R_s$. By extension $f_0 \propto R_s$. (equation 1). Furthermore, experimental evidence shows that there is negligible dependence of the tag substrate, antenna, capacitor plate, electrode material, and IC on their chemical environment, and thus $\Delta R \approx \Delta R_s$ (FIG. 8D).

Figure 7B:
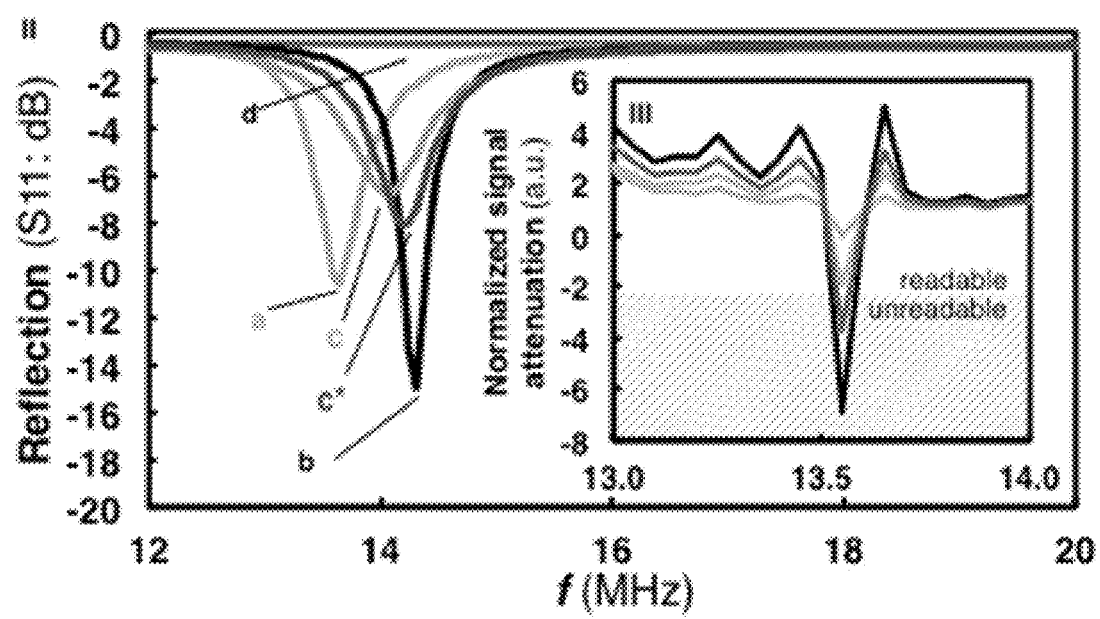
FIG. 7B shows averaged traces of frequency responses of (a) unmodified tags, (b) disrupted tags, (c) modified sensor tags before exposure to cyclohexanone, and (c*) modified sensor tags during exposure to cyclohexanone, and (d) single trace of frequency response in the absence of any tags. The insert shows normalized, frequency-dependent smartphone RF-signal attenuation of (a), (b), (c), and (c*).

FIG. 7B illustrates the relationship between $f_0$ and $R_s$ for a series of tags modified according to Sensing Method 1. A commercially available tag has $R_s$=0.5Ω and $f_0$=13.65±0.01 MHz (curve a). Disrupting a connection between the capacitor and IC results increases $R_s$ to 25 MΩ and increases $f_0$ to 14.30±0.01 MHz (curve b). Introduction of a chemiresistive material that bridges capacitor and IC by drawing at $R_s$=30 kΩ decreases $f_0$ to 14.10±0.01 MHz (curve c). Subsequent exposure to saturated vapor of cyclohexanone increases $R_s$ for example, from 30 kΩ to 70 kΩ and is accompanied by a shift in $f_0$ from 14.10±0.01 MHz to 14.20±0.01 MHz (curve d).

FIG. 7A shows two-step modification of tags with variable resistors. FIG. 7B shows averaged traces (solid, bold) of frequency responses collected in septuplet (translucent, narrow traces) of: (a) unmodified tags, $R_s \approx$0.5Ω; (b) disrupted tags, $R_s \approx$25 MΩ; (c) modified sensor tags before exposure to cyclohexanone (equilibrium vapor pressure at RT), $R_s \approx$30 kΩ; (c*) modified sensor tags after exposure to cyclohexanone (equilibrium vapor pressure at RT) for one minute, $R_s \approx$70 kΩ; (d) single trace of frequency response in the absence of any tags. The insert shows normalized, frequency-dependent smartphone RF-signal attenuation (backscatter modulation) of (a), (b), (c), and (c*).

Figure 8A:
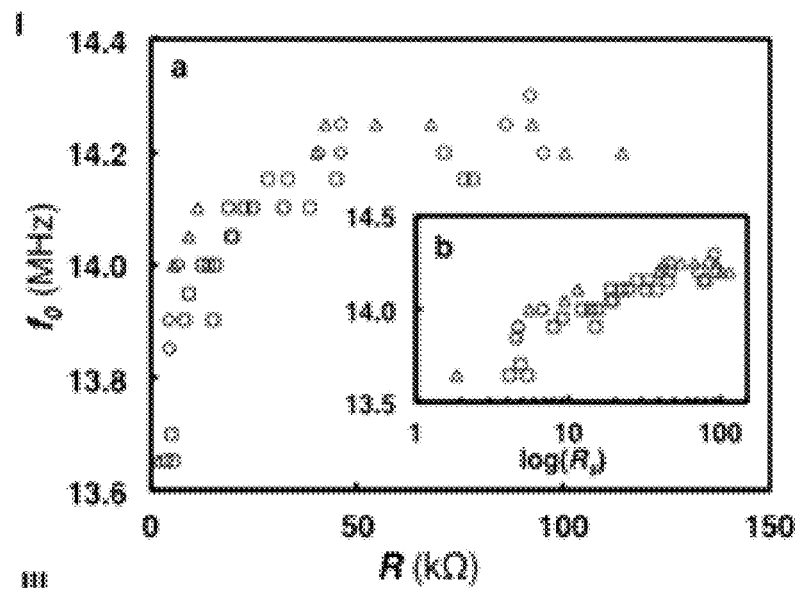
FIG. 8A shows correlation of the resonant frequency behavior of functionalized tags, compared to their readability by an NFC-enabled smartphone (blue=readable by Google Nexus S; red=unreadable by Google Nexus S).
Figure 8B:
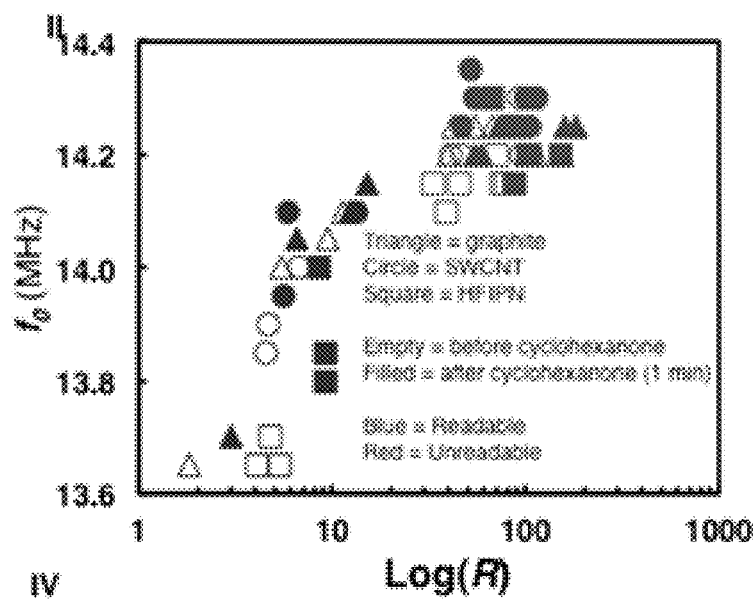
FIG. 8B shows correlation of the resonant frequency behavior of functionalized tags before (empty) and after (filled) exposure to cyclohexanone, compared to their readability by an NFC-enabled smartphone (blue=readable by Google Nexus S; red=unreadable by Google Nexus S).
Figure 8C:
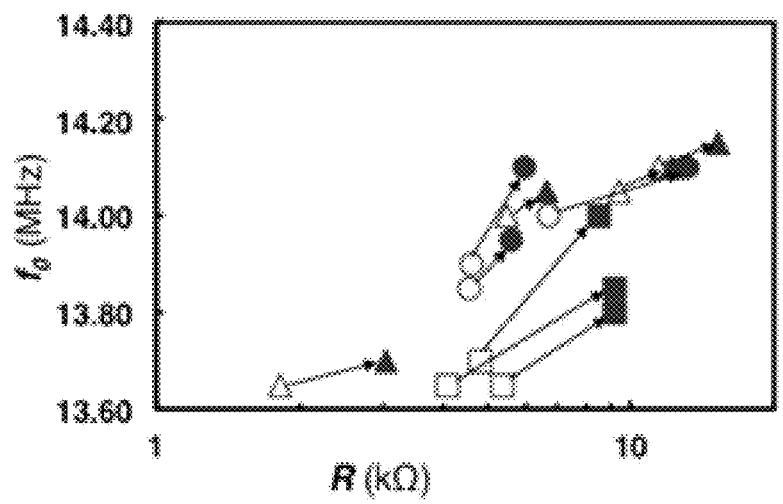
FIG. 8C shows correlation of the resonant frequency behavior of tags before (empty) and after (filled) exposure to cyclohexanone, compared to their readability by an NFC-enabled smartphone (blue=readable by Google Nexus S; red=unreadable by Google Nexus S).
Figure 8D:
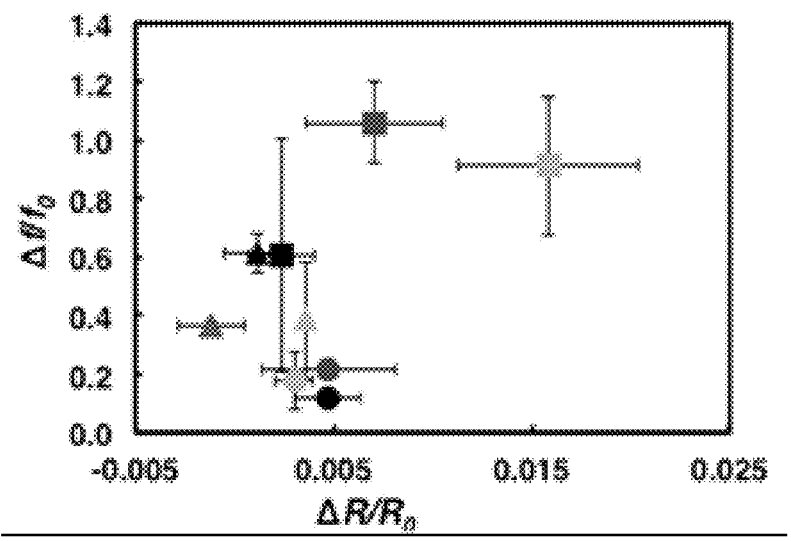
FIG. 8D shows comparison of the normalized change in resonant frequency to the normalized change in resistance of tags drawn at 10 kΩ (light blue), 50 kΩ (red), and 100 kΩ (black).
Figure 9:
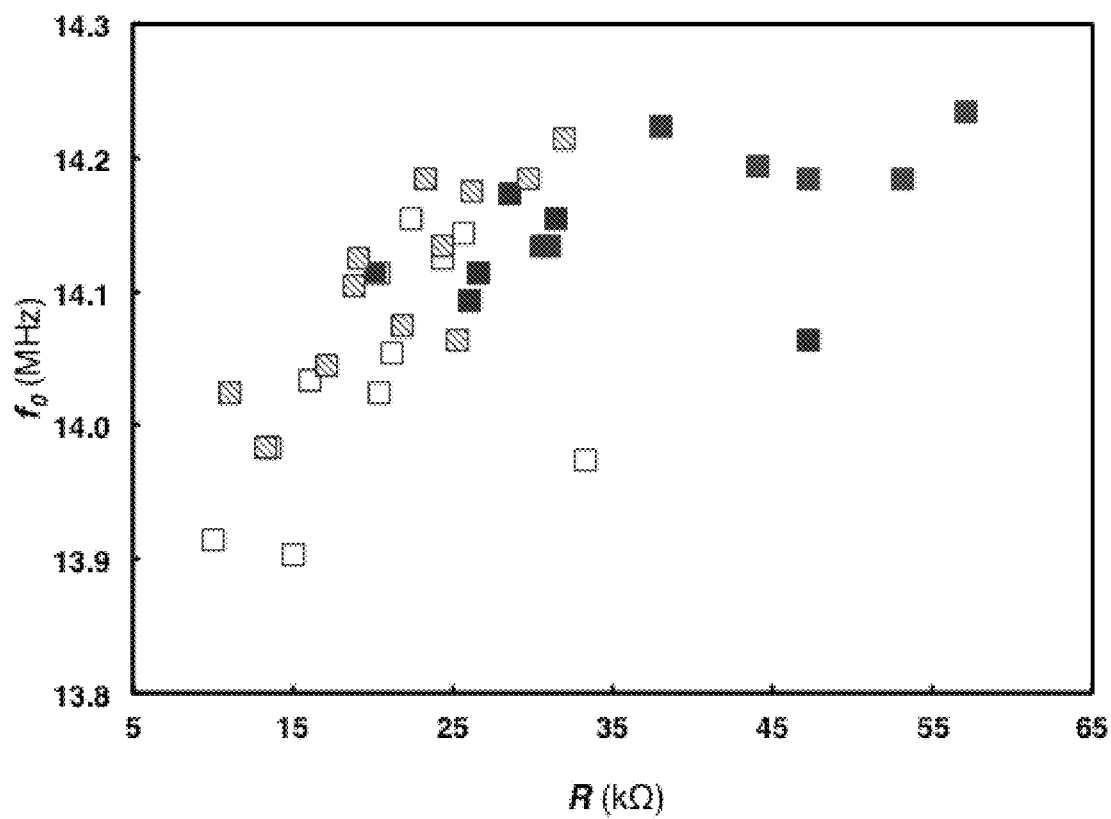
FIG. 9 shows correlation of the resonant frequency behavior of tags functionalized with a cyclohexanone sensor before (empty), during (filled), and after (hashed) exposure to cyclohexanone, compared to their readability by an NFC-enabled smartphone (blue=readable by Google Nexus S and Samsung Galaxy S4; Purple=readable by Google Nexus S and unreadable by Samsung Galaxy S4; red=unreadable by Google Nexus S).

FIGS. 8A-8D show the correlation between the readability of the chemiresistive tags by a Google Nexus-S smartphone as a function of $f_0$ and $R_s$ for three different chemiresistive materials (9B pencil, SWCNTs, and a 4:1 (mass) blend of 2-(2-Hydroxy-1,1,1,3,3,3-hexafluoropropyl)-1-naphthol (HFIPN) with SWCNTs. FIG. 8A shows Correlation of the resonant frequency behavior of tags functionalized with 9B pencil lead (triangle), SWCNT (circle), and 4:1 wt % HFIPN:SWCNT (square) sensors with $R_s$=1.5 kΩ-150 kΩ to their readability (red=unreadable; blue=readable) with a smartphone. FIG. 8B shows correlation of the resonant frequency behavior of functionalized tags before (empty) and after (filled) exposure to cyclohexanone (equilibrium vapor pressure at RT) for one minute to their readability with a smartphone. FIG. 8C shows correlation of the resonant frequency behavior of tags before (empty) and after (filled) exposure to cyclohexanone (equilibrium vapor pressure at RT) for one minute to their readability with a smartphone; arrows indicate vector movement of individual sensors. FIG. 8D shows comparison of the normalized change in resonant frequency to the normalized change in resistance of tags drawn at 10 kΩ (light blue), 50 kΩ (red), and 100 kΩ (black). FIGS. 8A-8D show that they all move in the same general direction and HFIPN/SWCNT moves the farthest (has the longest vector arrows).

These features of the sensing scheme can be exploited by taking advantage of the finite smartphone dynamic transmission frequency range. When the resonant frequencies of the tag insufficiently overlap with the dynamic transmission frequency range, the tag cannot be read by the smartphone, and vice versa. Unmodified tags have a resonant frequency of 13.65 MHz±0.01 MHz and disrupted tags have a resonant frequency of 14.20 MHz±0.01 MHz. When a chemiresistor is applied, the $f_0$ shifts to lower frequency. As more sensing material is applied, more conductive pathways form, and $R_s$ decreases, further lowering the frequency at which the tag resonates. The tag can then be made into a turn-off sensor by drawing a sensor that causes the tag to resonate within, but near the edge of the readable range of the smartphone. When the chemiresistor is exposed to an analyte, $R_s$ increases, thereby increasing $f_0$ to a value outside of the dynamic transmission frequency range of the smartphone, effectively entering into an "off" state. Removal of the analyte leads to the recovery of the sensor to its original value of $R_s$, bringing $f_0$ within the dynamic transmission frequency range of the smartphone, effectively returning to an "on" state.

Figure 10:
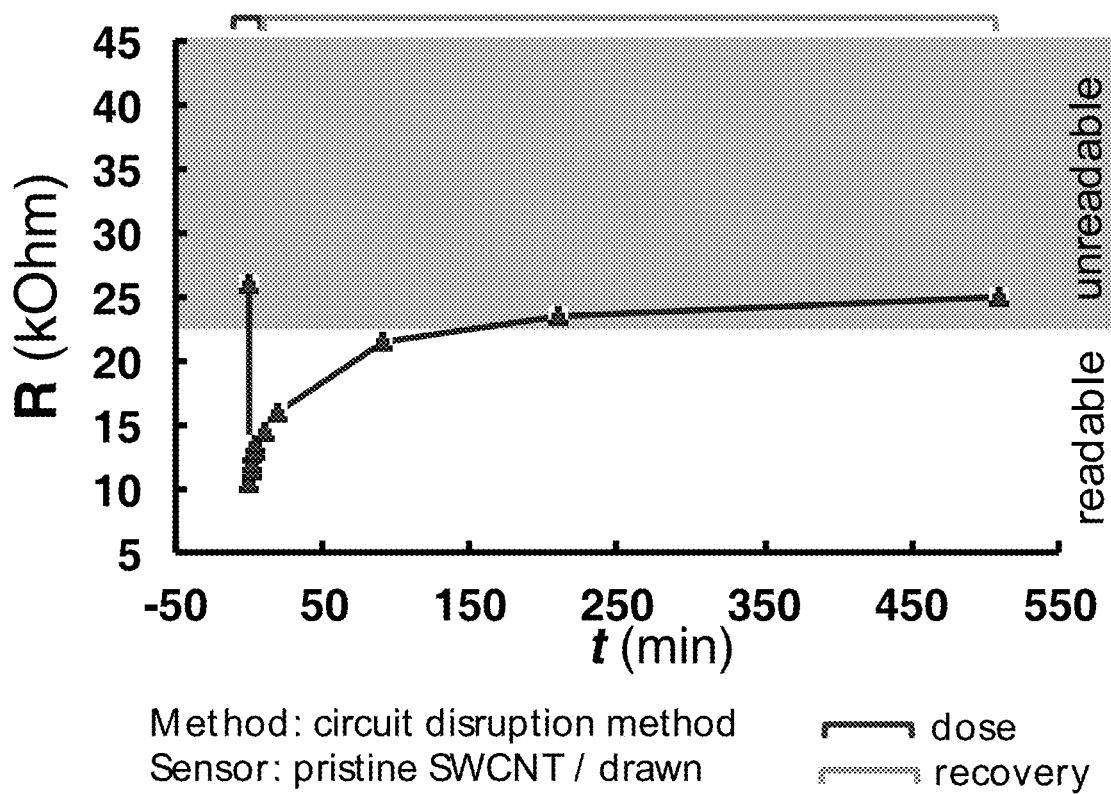
FIG. 10 illustrates the readability of a commercial RFID tag with a pristine single-walled carbon nanotube sensor when exposed to nitric acid vapors.

FIG. 10 illustrates the readability of a commercial RFID tag (Texas Instruments Tag-It HF-1) modified according to Sensing Method 1 with a pristine single-walled carbon nanotube sensor, correlated with resistance of the sensing material before and after one exposure to nitric acid vapor.

Figure 11:
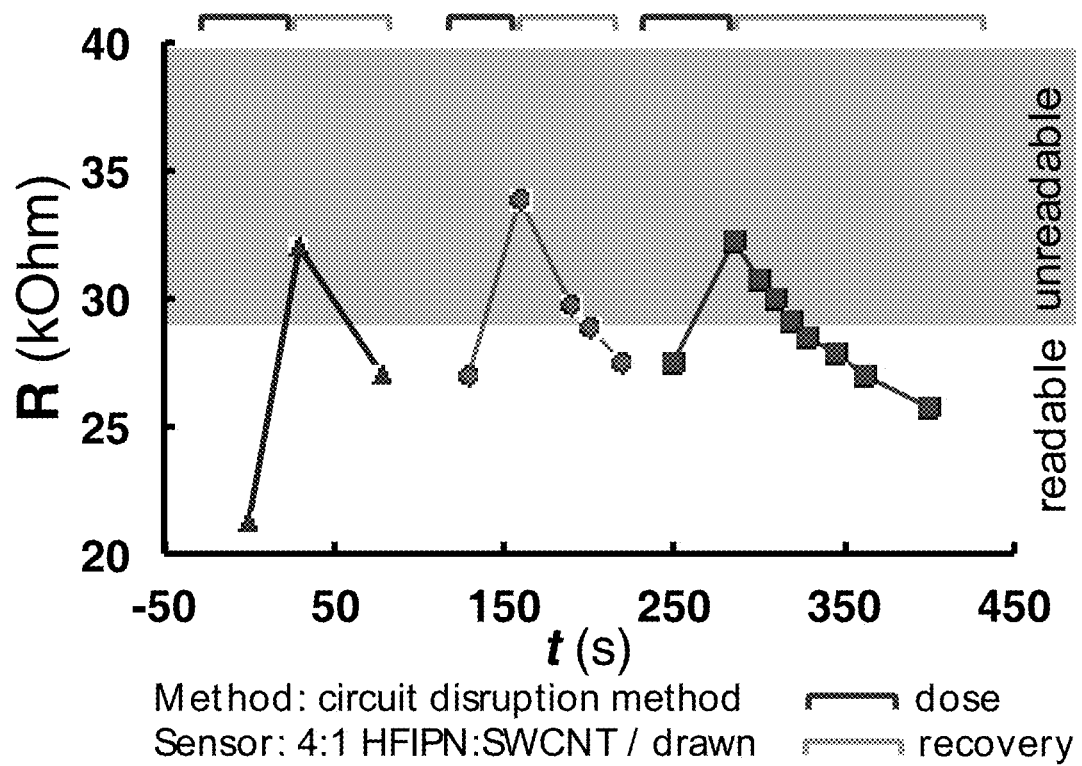
FIG. 11 illustrates the readability of a commercial RFID tag with a cyclohexanone sensor when cycled between exposure to cyclohexanone and air (×3).

FIG. 11 illustrates the readability of a commercial RFID tag (Texas Instruments Tag-It HF-1) modified according to Sensing Method 1 with a cyclohexanone sensor, correlated with resistance of the sensing material before and after three exposures to cyclohexanone vapor.

Figure 12:
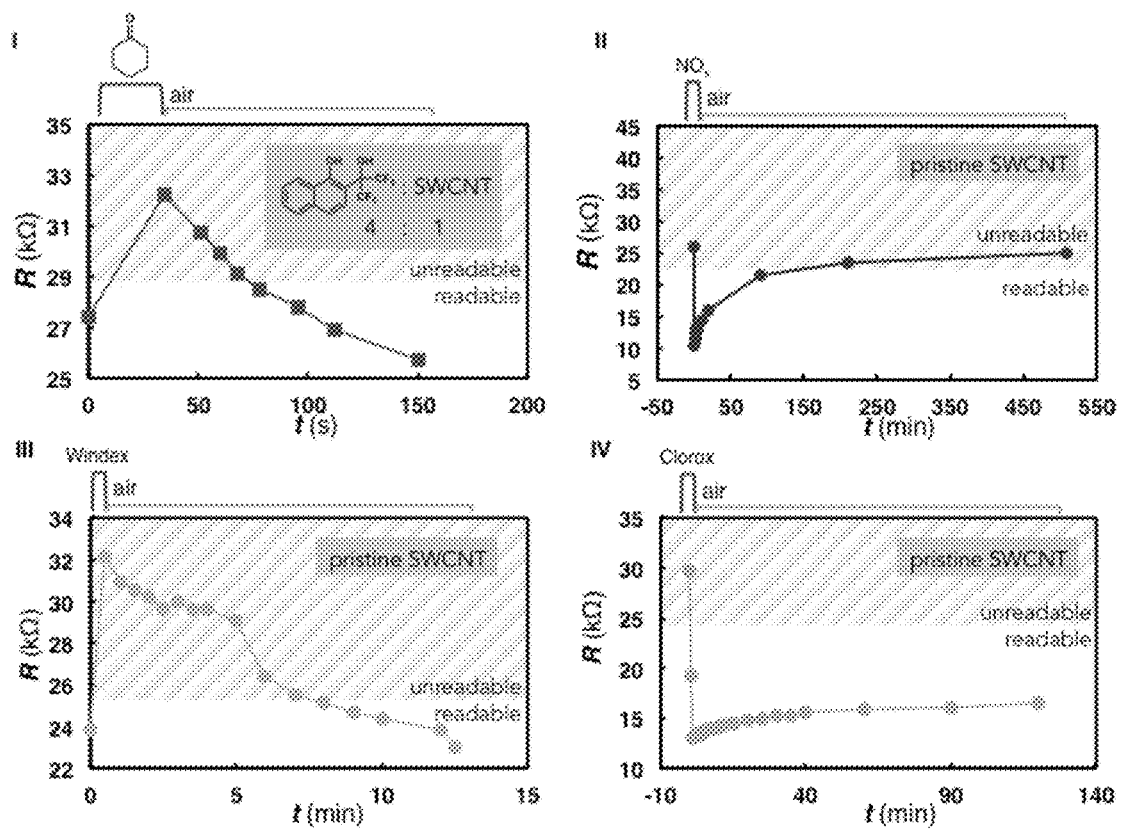
FIG. 12 shows turn-off sensing in response to exposure to (I) cyclohexanone and (III) Windex vapors.
Figure 13:
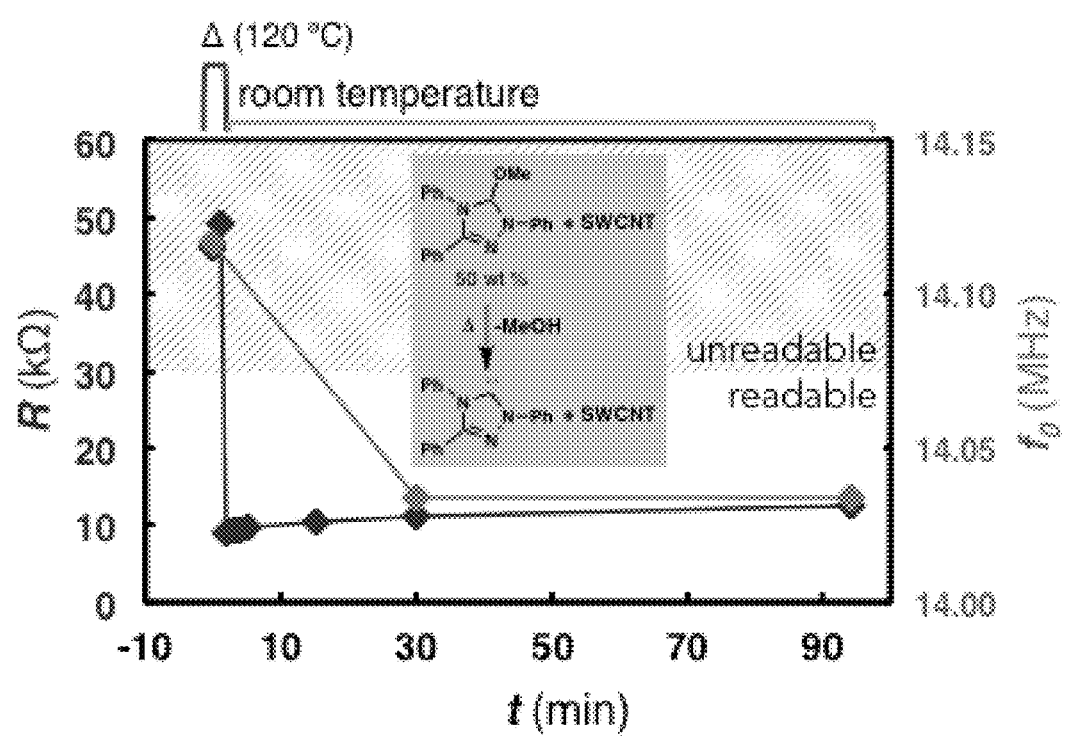
FIG. 13 shows turn-on sensing in response to exposure to heat (120° C. for 1 minute).
Figure 14:
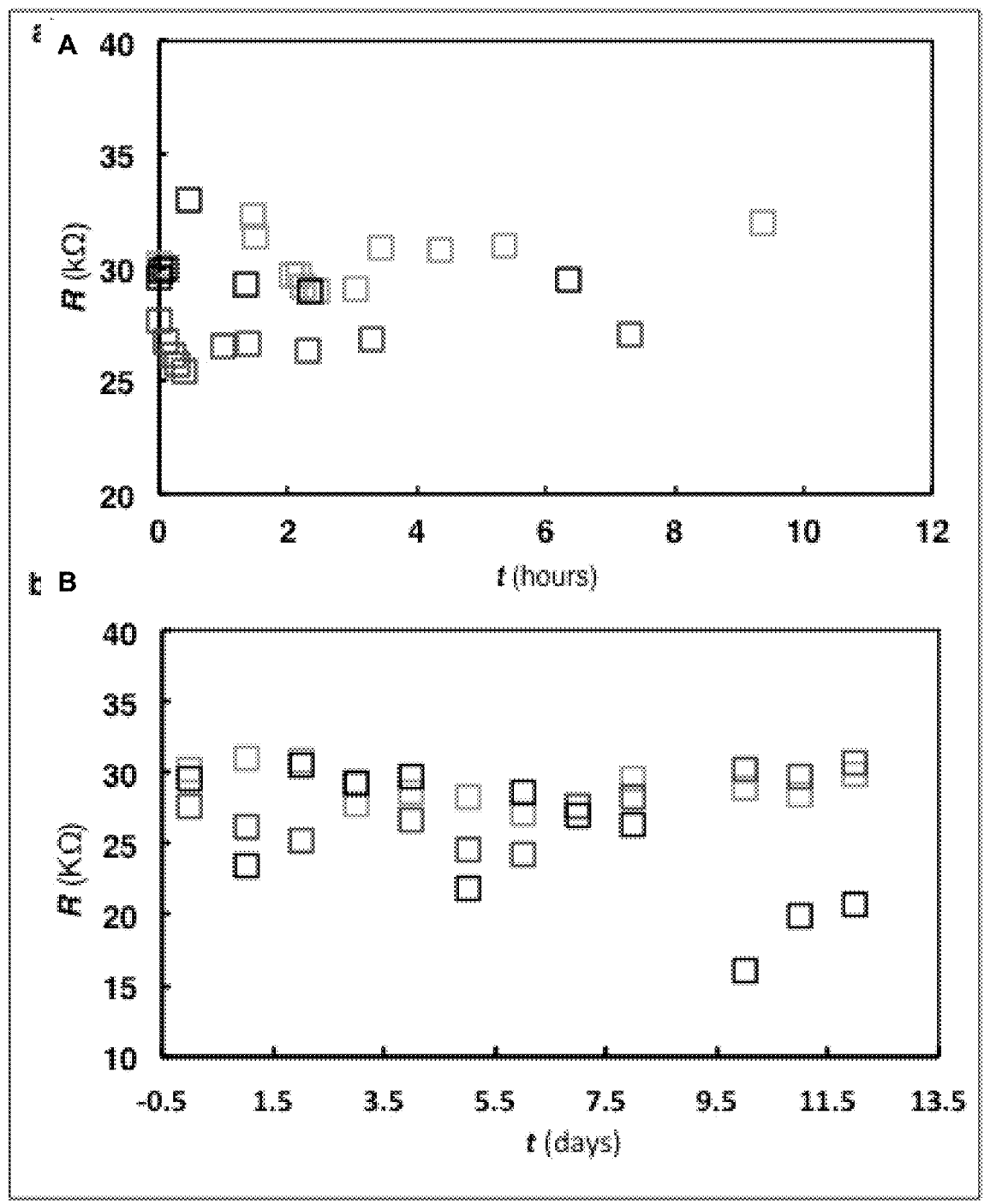
FIG. 14 shows stability 4:1 wt % 2-(2-Hydroxy-1,1,1,3,3,3-hexafluoropropyl)-1-naphthol (HFIPN): single-walled carbon nanotube (SWCNT) functionalized sensor tags to ambient conditions over (a) hours and (b) days.
Figures 15A, 15B:
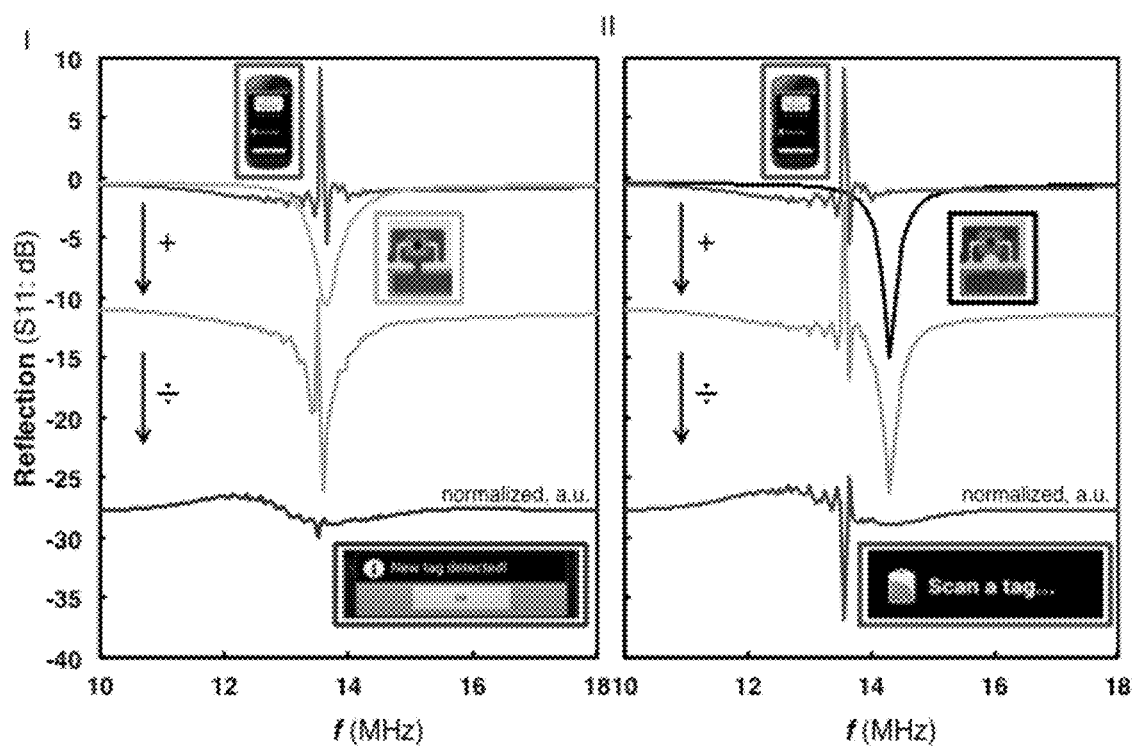
FIG. 15A demonstrates that a smartphone signal (purple trace) couples to an unmodified tag (grey trace), to give the modulated signal (orange trace), which can be analyzed by normalization to construct a backscatter signal modulation trace (blue trace), which indicates that the tag is readable.
FIG. 15B demonstrates that a smartphone signal (purple trace) couples to a modified tag (black trace) to give the modulated signal (orange trace), which can be analyzed by normalization to construct a backscatter signal modulation trace (red trace), which indicates that the tag is unreadable.
Figure 16:
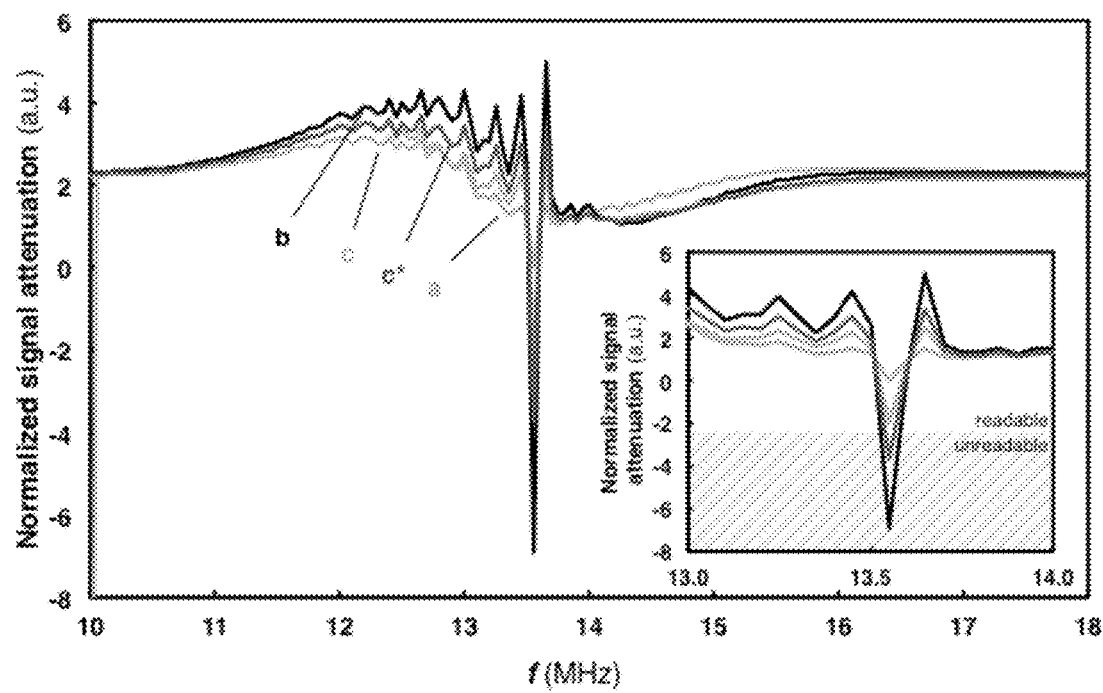
FIG. 16 shows normalized backscatter modulation traces of (a) unmodified tags, (b) disrupted tags, (c) modified sensor tags before exposure to cyclohexanone, and (c*) modified sensor tags during exposure to cyclohexanone.
Figure 17:
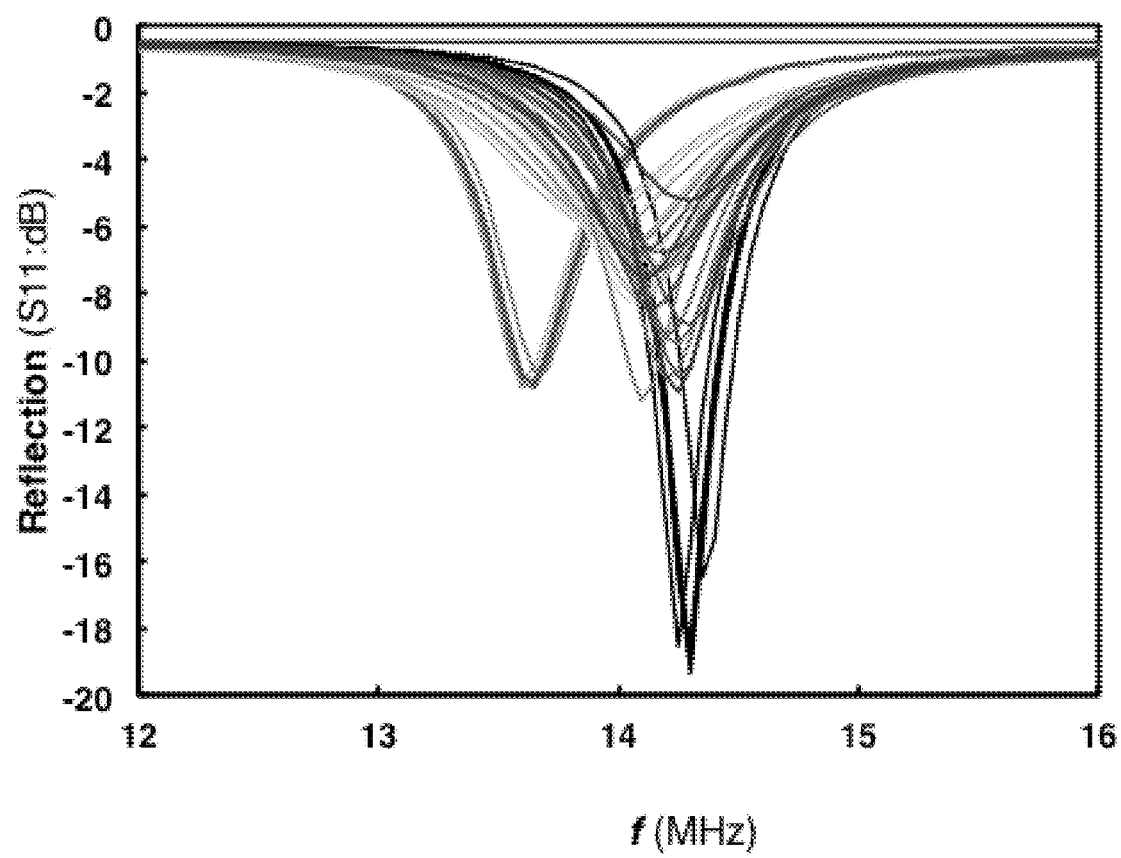
FIG. 17 shows good tag-to-tag reproducibility.

FIG. 12 shows sensor responses of tags exposed to respective analytes at equilibrium vapor pressures at RT. FIG. 12 shows turn-off of (I) cyclohexanone and (III) Windex; FIG. 12 shows turn-on of (II) $NO_x$ and (IV) Clorox. FIG. 14 shows stability 4:1 wt % HFIPN:SWCNT functionalized sensor tags to ambient conditions over time.

Fabrication and Characterization of CARDs

A simple two-step modification procedure can be used to make commercial NFC tags chemically sensitive (FIG. 18). FIG. 18 depicts the principle of Sensing Method 3. First, the electronic circuit of the tag was disrupted, rendering the tag unreadable, by removing a section of the conductive aluminum that connects the IC to the capacitor with a hole-puncher. Then, the LCR circuit was re-completed with conductive nano-carbon-based chemiresponsive materials deposited by mechanical abrasion (FIG. 18). Chemical selectivity in sensing was achieved by harnessing the established properties of chemiresponsive materials. See, Mirica K A, Weis J G, Schnorr J M, Esser B, Swager T M (2012) Mechanical drawing of gas sensors on paper. *Angew Chemie Int Ed* 51:10740-10745, Mirica K A, Azzarelli J M, Weis J G, Schnorr J M, Swager T M (2013) Rapid prototyping of carbon-based chemiresistive gas sensors on paper. *Proc Natl Acad Sci USA* 110: E3265-E3270, and Miyata Y, Maniwa Y, Kataura H (2006) Selective oxidation of semiconducting single-wall carbon nanotubes by hydrogen peroxide. *J Phys Chem B* 110:25-29, each of which is incorporated by reference in its entirety.

Figure 22:
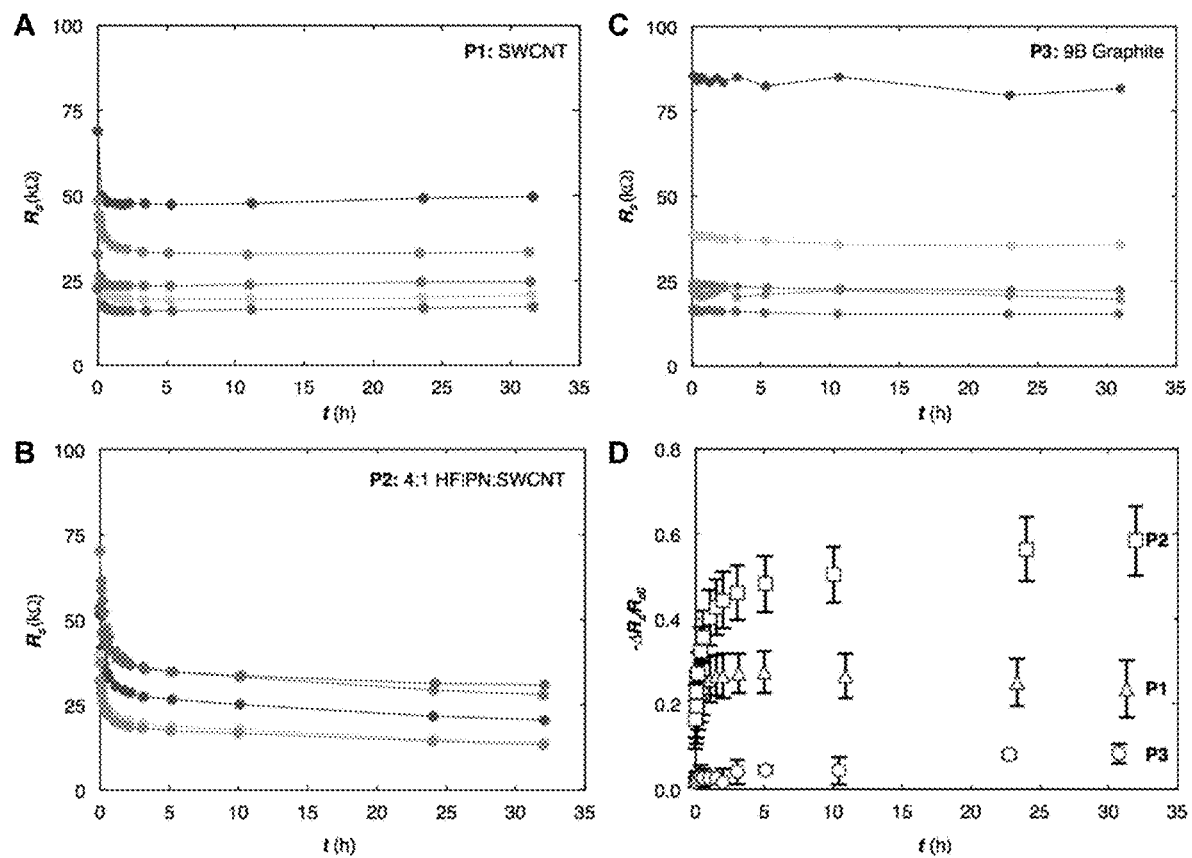
FIG. 22 shows CARD $R_s$ drifts predictably. CARDs (n=5) made by drawing (A) P1, (B) P2, and (C) P3 exhibit predictable drift characteristics across a range of initial $R_s$ values. Graph D shows Normalized change in resistance as a function of time for CARDs corresponding to (A) (squares), (B) (triangles), and (C) (circles).
Figure 23:
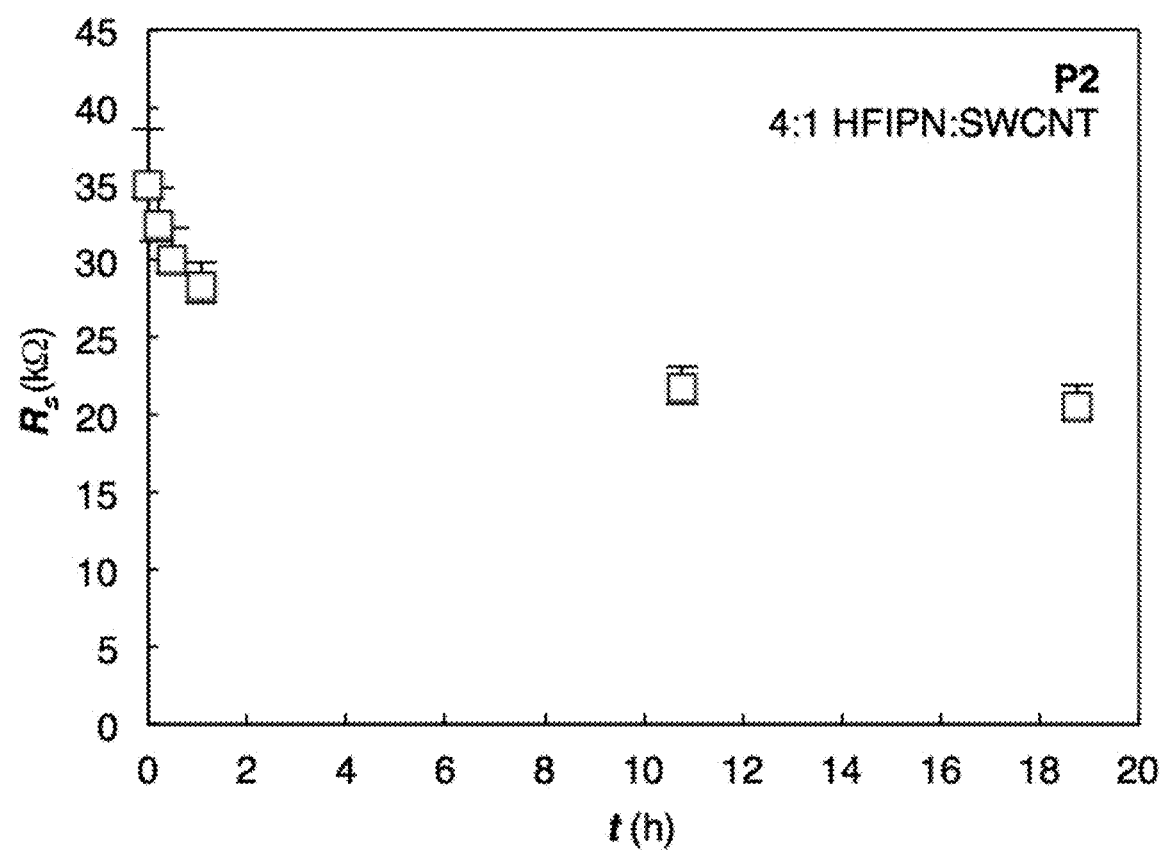
FIG. 23 shows CARDs can be fabricated to a desired $R_s$ range. $R_s$ drift of CARD-2 drawn as close to initial $R_s$=35 kΩ as possible (n=9) with P2. Initial average $R_s$=35 k+4 kΩ. Final average $R_s$=21 kΩ+1 kΩ. Error bars represent standard deviation from the average for nine distinct tags.

This study employed two different solid-state chemiresponsive materials-PENCILs (Process-Enhanced Nanocarbon for Integrated Logic)—that can be conveniently drawn on a variety of surfaces using an established technique. See, Mirica K A, Azzarelli J M, Weis J G, Schnorr J M, Swager T M (2013) Rapid prototyping of carbon-based chemiresistive gas sensors on paper. *Proc Natl Acad Sci USA* 110: E3265-E3270, which is incorporated by reference in its entirety. For sensing ammonia ($NH_3$) and hydrogen peroxide ($H_2O_2$)— common industrial hazards that can be used in improvised explosives-pristine single-walled carbon nanotubes (SWCNTs) compressed in the form of a pencil 'lead' were chosen (P1) (see, Mirica K A, Weis J G, Schnorr J M, Esser B, Swager T M (2012) Mechanical drawing of gas sensors on paper. *Angew Chemie Int Ed* 51:10740-10745, and Miyata Y, Maniwa Y, Kataura H (2006) Selective oxidation of semiconducting single-wall carbon nanotubes by hydrogen peroxide. *J Phys Chem B* 110:25-29, each of which is incorporated by reference in its entirety); this material exhibits a well-characterized, dose-dependent chemiresistive response towards these analytes. A solid composite comprising a 4:1 (wt:wt) blend of 2-(2-Hydroxy-1,1,1,3,3,3-hexafluoropropyl)-1-naphthol (HFIPN) with SWCNTs generated via solvent-free mechanical mixing within a ball mill (P2) was selected because this material exhibits high selectivity and sensitivity for cyclohexanone ($C_6H_{10}O$) vapors (a common constituent of plastic explosives) (see, Mirica K A, Azzarelli J M, Weis J G, Schnorr J M, Swager T M (2013) Rapid prototyping of carbon-based chemiresistive gas sensors on paper. *Proc Natl Acad Sci USA* 110: E3265-E3270, Frazier K M, Swager T M (2013) Robust cyclohexanone selective chemiresistors based on single-walled carbon nanotubes. *Anal Chem* 85:7154-7158, and Cox J R, Miller P, Swager T M (2011) Interrupted energy transfer: highly selective detection of cyclic ketones in the vapor phase. *J Am Chem Soc* 133:12910-12913, each of which is incorporated by reference in its entirety). HB pencil 'lead' (P3) was chosen as a negative control because it shows a negligible response towards the concentrations of analytes used in this study. These materials exhibit predictable drift and consistent stability in their electrical resistance ($R_s$) when deposited on the surface of the NFC tags (FIGS. 22 and 23).

Figure 24A:
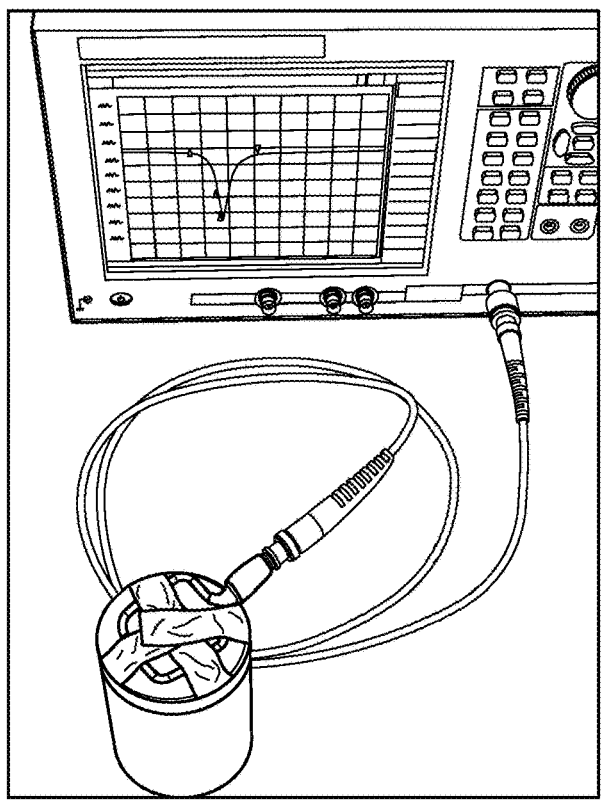
FIG. 24 shows radio frequency reflection coefficient ($S_{11}$) measurements are performed with a loop-probe connected to a vector network analyzer. Photo A shows vector network analyzer shown connected to loop probe affixed to a jar cap on an empty jar. Photo B shows image of the custom-made loop probe used in this study, taped to the top of a jar cap with electrical tape. Photo C shows image of a CARD placed on the inside of a jar cap using double-sided tape.
Figure 24B:
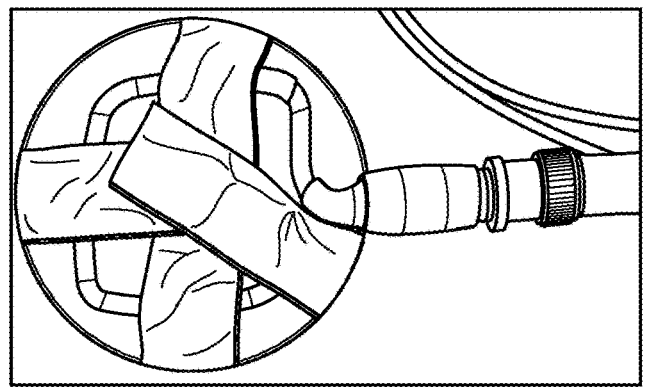
Figure 24C:
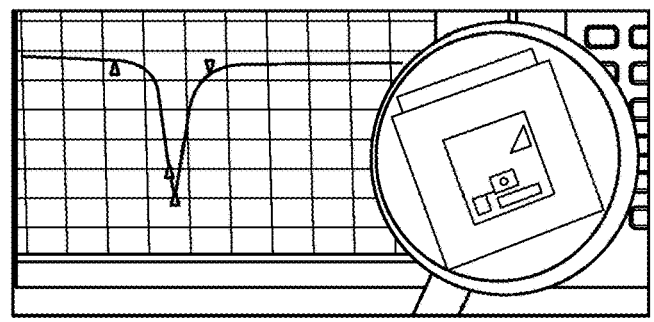

A network analyzer was employed to determine $f_0$ and Q of the NFC tags at various stages of modification by measuring the radio-frequency reflection coefficient, $S_{11}$ (FIGS. 19 and 24). See, Cole P, Ranasinghe D, Jamali B (2004) Coupling relations in RFID systems II: practical performance measurements (2003) AUTO-ID-CENTRE, ADE-AUTOID-WH-003, which is incorporated by reference in its entirety. In tandem, SGS4 was employed to test the readability of the tags ("on"/"readable" and "off"/"unreadable") and a multimeter to estimate the electrical resistance ($R_s$) of the connection between the capacitor and the integrated circuit within the NFC tag. FIG. 19 Graph A shows a plot that exhibits six notable features. First, in the absence of any device, the $S_{11}$ spectrum displays a flat baseline (FIG. 19 Graph A-1). Second, unmodified NFC tags ($R_s$=0.3 Ω+0.0Ω) are SGS4-readable ("on") and display a resonant frequency of 13.67 MHz+0.01 MHz and Q=35±1 (FIG. 19 Graph A-2). Third, tags where the electrical connection between the integrated circuit and the capacitor has been disrupted by hole punching ($R_s$=23.3 MΩ±0.8 MQ) are SGS4-unreadable ("off") and display $f_0$=14.29 MHz+0.01 MHz and Q=85±2 (FIG. 19 Graph A-3). Fourth, when the electrical circuit is recompleted using P2, the resulting CARD-2 ($R_s$=16.5 k+1.0 kΩ) becomes SGS4-readable ("on"), and has $f_0$=14.26 MHz+0.02 MHz and Q=21±1 (FIG. 19 Graph A-4). Fifth, when this CARD-2 is exposed to vapors of cyclohexanone (~5000 ppm), a significant change in both $f_0$ and Q is observed. After five seconds of exposure, $f_0$ shifts to 14.30 MHz+0.01 MHz and Q increases to 32±1 (FIG. 19 Graph A-5), and the tag becomes SGS4-unreadable ("off"). After one minute, $f_0$ remains at 14.30±0.00 MHz; Q increases to 51±2 (FIG. 19 Graph A-6), and the tag remains SGS4-unreadable ("off").

Figure 27:
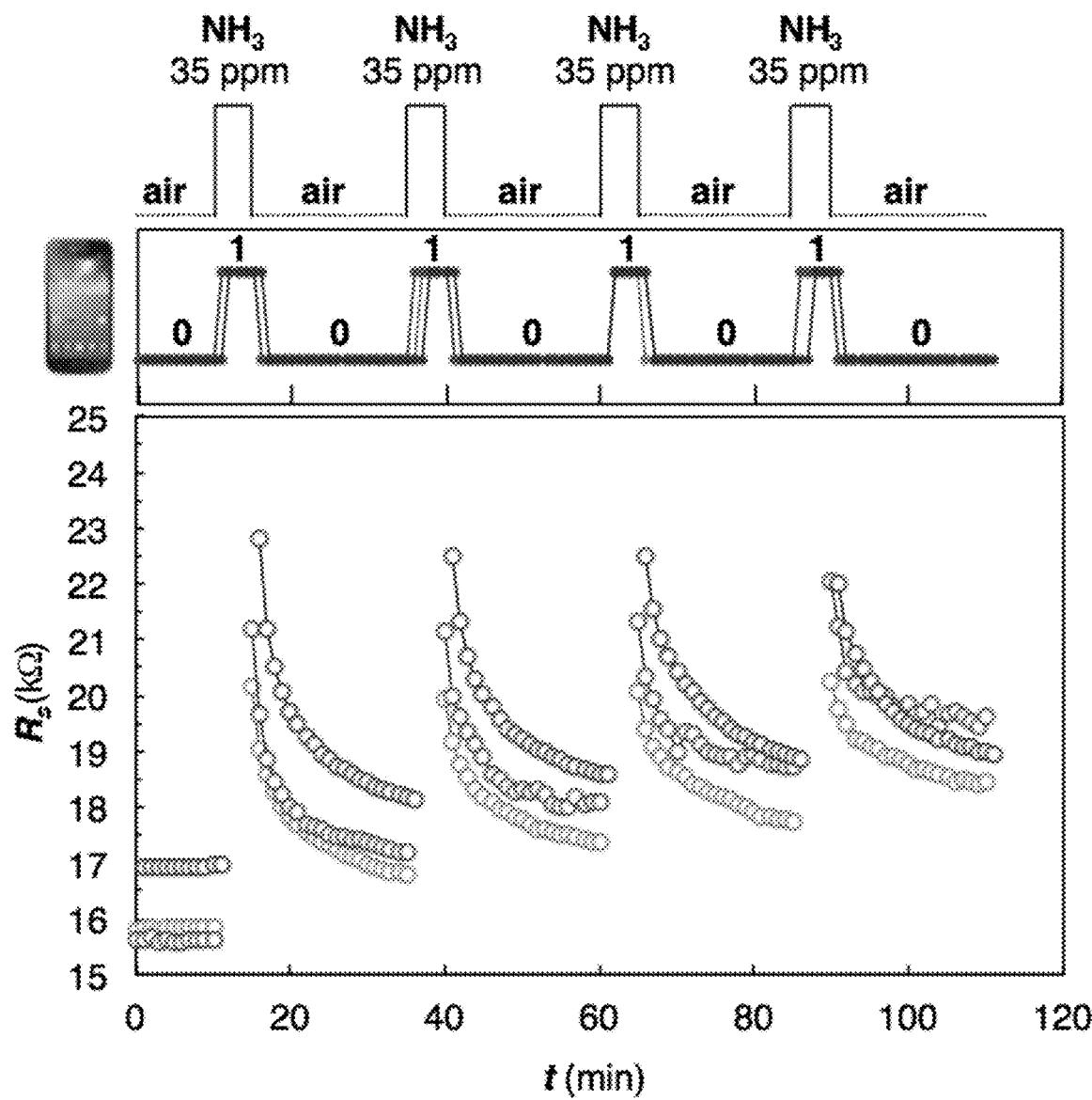
FIG. 27 shows CARD-1A displays reversible behavior to multiple exposures of $NH_3$ (35 ppm). Response of CARD-1A (n=3) to four 5 min exposures of $NH_3$ (35 ppm) at 20 min intervals as monitored with a SGS4 (top, lines) and a multimeter (bottom, open circles).

Readability of CARDs by the smartphone can be rationalized by estimating the percent of incident power transferred ($P_t$) from the smartphone to the tag or CARD (FIGS. 19B and 27). For the purposes of this study, the distance of the smartphone to the CARD and the orientation of the smartphone with respect to the CARD were kept constant; however in a non-laboratory setting, distance and orientation would have to be taken into consideration. The commercial NFC tag (FIG. 19 Graph B-2) absorbs nearly 77% of the RF signal delivered from the smartphone. The disrupted circuit, however, absorbs only 14% of the RF signal from the phone; this amount is insufficient for effective smartphone-tag communication and the tag is unreadable by the SGS4 (FIG. 19 Graph B-3). Incorporation of a chemiresponsive material from P2 into this tag creates CARD-2, resulting in the amount of absorbed RF signal increasing to 23%—a sufficient amount of power transfer to enable RF communication ("on") (FIG. 19 Graph B-4). Subsequent exposure of CARD-2 to $C_6H_{10}O$ decreases the absorbed RF signal to 19% and results in CARD-2 becoming unreadable by SGS4 (FIG. 19 Graph B-5). Prolonged exposure of CARD-2 to the analyte for one minute leads to a further decrease in absorbed RF signal from the phone (16%) (FIG. 19 Graph B-6). Thus, $P_t$ between smartphone and CARDs decreases with increasing R.

Semi-Quantitative Detection of Ammonia with a Smartphone and CARDs After establishing the correlation between $R_s$, $P_t$, and the readability by the smartphone, the ability of CARDs to detect and wirelessly communicate repeated chemical exposure to 35 ppm $NH_3$ gas was tested. To program CARDs (n=3) for $NH_3$, P1 was integrated with initial $R_s$=16.1 kΩ+0.6 kΩ into the LCR circuit using the modification method described in FIG. 18, resulting in CARD-1A. $R_s$ was measured and tested the SGS4 readability of CARD-1A in response to four consecutive exposures to 35 ppm $NH_3$ gas (FIG. 27). For clarity, FIG. 20 Graph A summarizes the effect of $NH_3$ (35 ppm) on the resistance and phone readability of a single CARD-1A. Within one minute of exposure to 35 ppm $NH_3$, CARD-1A experienced $\Delta R_s$=5.3 kΩ+0.7 kΩ and became unreadable (turned "off") when probed by the phone. Removal of $NH_3$ and recovery under ambient air led to a rapid recovery of $R_s$ and retrieval of phone readability of CARD-1A. After a 20 min recovery under ambient atmosphere, the $R_s$ of CARD-1A recovered to 17.4 kΩ+0.6 kΩ($\Delta R_s$=+1.2 kΩ+0.3 kΩ from the value of $R_s$ before exposure).

Figure 20:
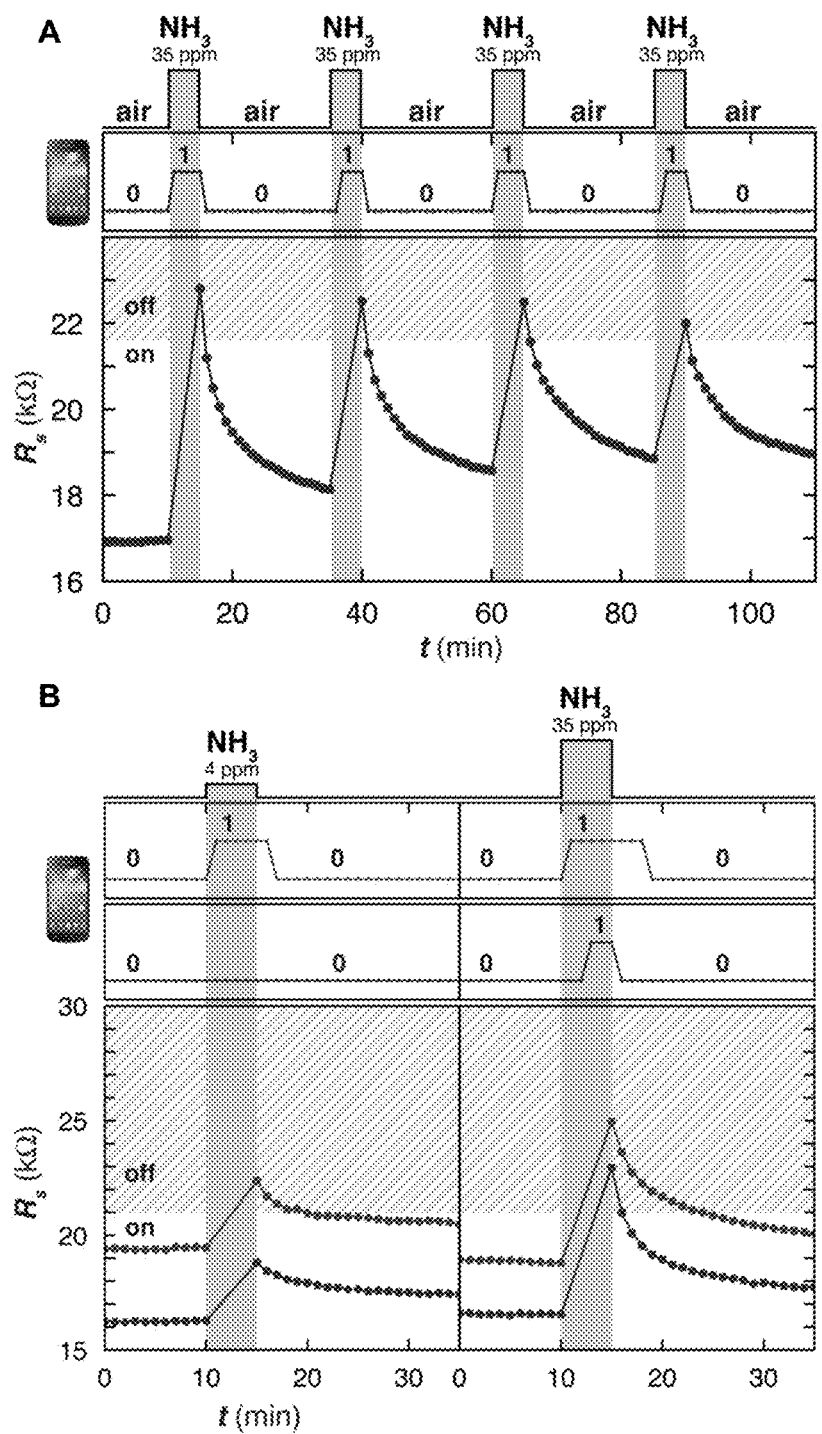
FIG. 20 shows CARDs programmed to detect different concentrations of analyte. Graph A shows response of CARD-1A to four 5 min exposures of $NH_3$ (35 ppm) at 20 min intervals as monitored with a SGS4 (top) and a multimeter (bottom). Shaded boundary indicates estimated $R_t$ based on the trace shown. Graph B shows response of CARD-1A (blue) and CARD-1B (orange) to a single 5 min exposure of $NH_3$ at two different concentrations (4 ppm & 35 ppm) as monitored with a SGS4 (top) and a multimeter (bottom). Shaded boundary indicates estimated $R_t$ based on the traces shown.

Correlating the readability of CARD-1A by SGS4 with $R_s$ enabled us to estimate that the "on"/"off" threshold ($R_t$) for P1 when exposed to $NH_3$ was 20.8 kΩ+1.0 kΩ. Below this critical value of $R_t$, CARD-1A was readable by the SGS4, and it is unreadable when $R_s>R_t$. The well-defined value of $R_t$ in the wireless communication between the smartphone and CARDs fabricated with P1, coupled with the established concentration-dependent response of SWCNTs to $NH_3$, enables semi-quantitation. To demonstrate this concept, two types of CARDs were fabricated in triplicate and designed to turn off in response to crossing different threshold concentrations of $NH_3$: 4 ppm (just below the threshold of human detection of $NH_3$ based on smell) (CARD-1B; initial $R_s$=19.2 kΩ+0.2 kΩ) and 35 ppm (NIOSH STEL) (CARD-1A; initial $R_s$=16.3 kΩ+0.5 kΩ) (FIG. 20 Graph B and Table 1). Prior to exposure to $NH_3$, both CARDs were readable by the phone. Exposure to 4 ppm $NH_3$ only turns CARD-1B "off," whereas exposure to 35 ppm $NH_3$ turns both CARDs "off." This concept is general: with sufficient information about the concentration-dependent response of the chemiresponsive sensing elements in the presence of the analytes of interest, CARDs can be programmed to turn "on" or "off" at the designated thresholds of various analytes.

TABLE 1

Estimated $R_t$ of CARDs employed in this study.

| Entry | FIG. | PENCIL | Analyte | n = | $R_t$ |
|---|---|---|---|---|---|
| A | 20A | P1 | $NH_3$ | 12 | 20.8 ± 1.0 |
| B | 20B | P1 | $NH_3$ | 9 | 21.6 ± 0.7 |
| C | 21A | P1 | $NH_3$ | 3 | 20.2 ± 0.5 |
| D | 21B | P1 | $H_2O_2/H_2O$ | 3 | 22.4 ± 2.4 |
| E | 21C | P2 | $C_6H_{10}O$ | 3 | 24.0 ± 1.8 |

Discrimination of Analytes with an Array of CARDs

The fabrication of arrays of CARDs containing different chemiresponsive materials can also enable the detection and discrimination of multiple analytes using NFC communication (FIG. 21). Three different sensing materials (P1-P3) that produce distinct $\Delta R_s$ upon interaction with $NH_3$ gas (35 ppm), cyclohexanone vapor (335 ppm), $H_2O_2$ vapor (~225 ppm), and $H_2O$ vapor (~30,000 ppm) were employed. An array of four types of CARDs (each type in triplicate) was produced and used to detect single exposures of the analytes. To detect $NH_3$, CARD-1A (initial $R_s$=16.3 k$\Omega$+0.6 k$\Omega$) was designed to turn "off" upon exposure to 35 ppm $NH_3$, and turn back "on" upon recovery under ambient conditions (FIG. 21 Graph A-1). Importantly, CARD-1A does not turn "off" in the presence of the other analytes at the concentrations tested (FIG. 21 Graph A-2,3,4).

To detect $H_2O_2$, a "turn-on" sensor having an initial condition of being "off" was fabricated by mechanically abrading P1 to obtain initial $R_s$=23.4 k$\Omega$+0.9 k$\Omega$ (CARD-1C). CARD-1C turned "on" and became readable by the SGS4 when it was exposed to the equilibrium vapor of $H_2O_2$ (35 wt. % in water), and turned back "off" as it recovered under ambient atmosphere (FIG. 21 Graph B-2). Although the exposures of CARD-1C to water, cyclohexanone, and $NH_3$ lead to small to moderate $\Delta R_s$ ($\Delta R_s$=+1.5 k$\Omega$+0.6 k$\Omega$ for water), these exposures did not invoke a change in its readability by SGS4 (FIG. 21 Graph B-1,3,4).

To detect cyclohexanone, a "turn-off" sensor CARD-2 with an initial condition of being "on" was fabricated by mechanical abrasion of P2 at initial $R_s$=18.9 k$\Omega$+0.6 k$\Omega$ on the surface of the tag. CARD-2 turned "off" within one minute of exposure to 335 ppm cyclohexanone (FIG. 21 Graph C-3). The readability of CARD-2 by SGS4 was reversible as it turned back "on" within one minute of recovery under ambient air. The value of $R_s$ for CARD-2, however, did not recover to its initial value of $R_s$; rather, it settled at $R_s$=15.3 k$\Omega$+0.9 k$\Omega$ after equilibrating for 10 minutes. This mismatch in $R_s$ may be due to solvent-assisted rearrangement of the sensing material. Importantly, although exposure of CARD-2 to $H_2O$, $H_2O_2$, and $NH_3$ produced small $\Delta R_s$ (FIG. 21 Graph C-1,2,4), they did not alter the readability of this sensor by the smartphone.

As a negative control, CARD-3 was fabricated by mechanical abrasion of P3 to obtain $R_s$=18.0 k$\Omega$+0.6 k$\Omega$. This tag remained readable and did not change its readability in response to analytes used in this example (FIG. 21 Graph D-1-4). This tag was an important component of an array-based sensing scheme because it validated the integrity of the reader-tag communication protocol and provided a static handle in a codification scheme.

Methods

Conversion of a Commercial NFC Tag into a Programmable CARD (Chemically Actuated Resonant Device)

Figure 25:
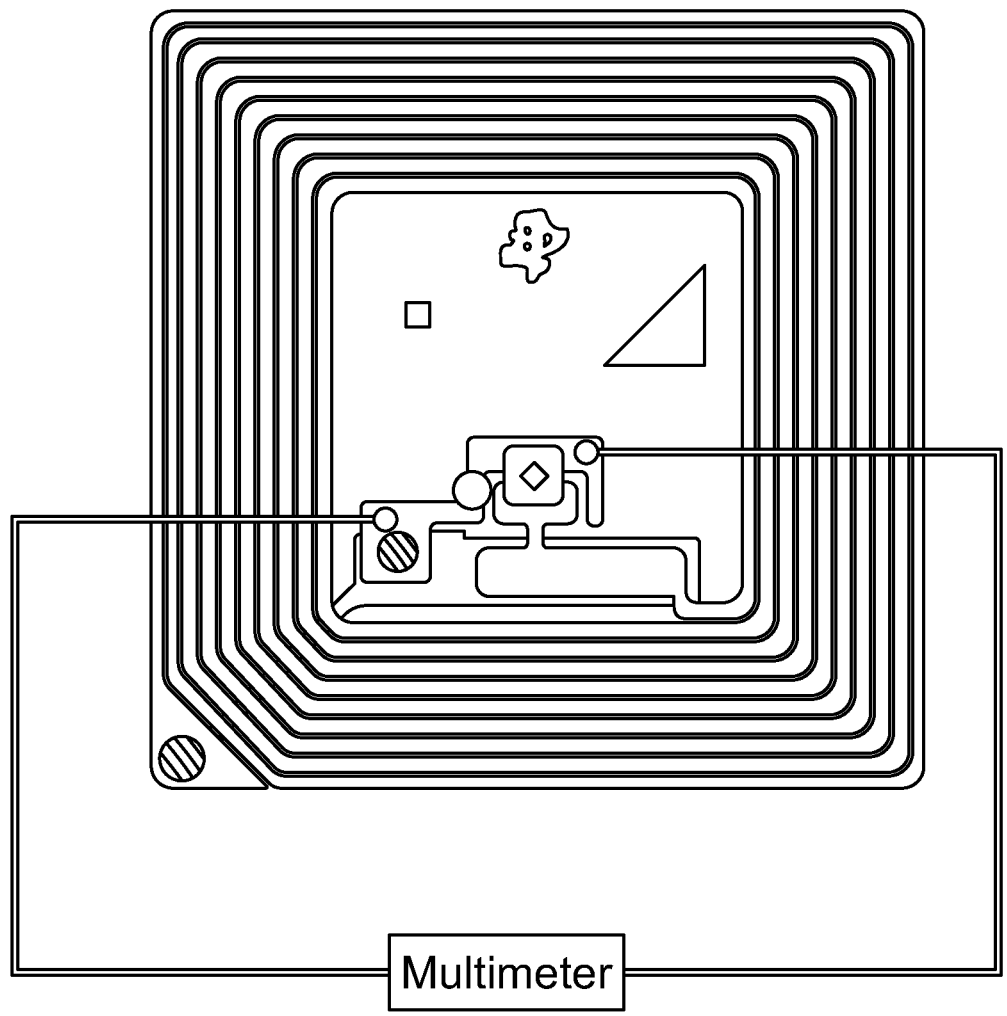
FIG. 25 shows CARD $R_s$ was measured with a multimeter. $R_s$ was measured using a multimeter by contacting the CARD at the locations depicted above.

The circuit of an NFC tag was disrupted at the location indicated in FIG. 18 using a circular hole puncher (Bead Landing™, hole diameter=2 mm). A hole was punched through the tag, effectively removing a portion of the conducting aluminum film (along with the underlying polymeric substrate) connecting the integrated circuit to the capacitor. The circuit was re-completed using the mechanical abrasion by drawing a line with an appropriate PENCIL to bridge the two disconnected ends of aluminum. See, Mirica K A, Azzarelli J M, Weis J G, Schnorr J M, Swager T M (2013) Rapid prototyping of carbon-based chemiresistive gas sensors on paper. *Proc Natl Acad Sci USA* 110: E3265-E3270, which is incorporated by reference in its entirety. An iterative process of mechanical abrasion of the PENCIL followed by measuring $R_s$ (FIG. 25) with a multimeter (Fluke 114 TRMS Multimeter) was repeated until the desired initial $R_s$ value was achieved. When P1-P3 are deposited on the surface of the NFC tag by mechanical abrasion, they exhibit predictable drift characteristics, which allowed for the drawing of tags to pre-determined specifications (FIGS. 22 and 23). To prevent potential inhalation of particulates generated by the abrasion of PENCIL on NFC tags, this process was carried out in a fume hood. The resulting device was allowed to equilibrate until a stable reading ($\Delta R_s$<0.2 k$\Omega$/10 min) was achieved (~30 min). All experiments were conducted within 5 h of making a CARD.

Programming a CARD-Induced Smartphone Response

A response that is unique to a specific tag can be invoked upon successfully establishing communication between the tag and the phone ("on"/"readable") by pre-programming a tag-phone relationship prior to fabrication of a CARD. This study employed the freely available app 'Trigger' (Egomotion Corp; 28 Aug. 2014) to establish the phone-tag relationship. First, the UID of a tag is registered with the smartphone by scanning it via NFC. Second, a task (or tasks) are assigned to that specific UID. For example, a task that can be achieved with the use of 'Trigger' is to open another application, such as a note-taking app, that has a pre-defined message written on it. Other possible tasks that can be invoked include opening the e-mail app with a pre-written message, opening a maps app that displays the current location of the smartphone, etc. By programming 'Trigger' to invoke a unique task for each unique tag UID, once the tag has been converted to a CARD, meaningful information about the CARDs chemical environment can be conveyed to the user. Although outside of the scope of this study, this strategy could be improved by creating a customized app that allows more sophisticated smartphone actions in a less cumbersome user-interface architecture.

Method for Determining Reflection Coefficient and Readability of CARDs with a Smartphone The reflection coefficient spectra ($S_{11}$) were collected with a network analyzer (Agilent E5061B). A loop probe was affixed to the outside of a jar cap (VWR, 250 mL) using electrical tape and a tag or CARD was placed on the inside of the same jar cap using double sided tape (FIG. 24). Two jars were used for the experiment: one that was empty (i.e. filled with ambient air), and one that contained cyclohexanone (10 mL) and filter paper. The reflection coefficient spectra was measured and recorded once when the cap was on the empty jar, once after the cap was on the jar containing cyclohexanone for 5 s, and once after the cap was on the jar containing cyclohexanone for 1 minute (FIG. 19 Graph A).

The readability of the tag or CARD was determined by removing the tag from the jar cap, placing it on a piece of open-cell foam (thickness=4.5 cm), and approaching the sensor tag with a Samsung Galaxy S®4 running Android™ version 4.3 with 'NFC Reader' application (Adam Nyback; 5 Jul. 2013) open, held with its back parallel to the sensor tag. A sensor tag was considered "on"/"readable" if the UID could be retrieved within 5 seconds or less of holding the smartphone at ~2.5 cm distance above the tag. Conversely, the tag was considered "off"/"unreadable" if the UID could not be retrieved under the same conditions. All measurements were performed with the phone oriented such that the parallel plate capacitor of the CARD is perpendicular to the long edge of the phone. The phone was held parallel to the surface on which the tag rested.

Correlating Effects of Chemical Exposure on $R_s$ and Smartphone Readability of the CARD A CARD was attached to one side of a plastic petri dish using double sided tape. The $R_s$, was determined by contacting the CARD at the indicated points using a multimeter (Fluke 114 TRMS Multimeter). The readability of the CARD by SGS4 was determined as described above. Conversely, the CARD was considered "off" if the UID could not be retrieved under the same conditions.

First, $R_s$ and readability were monitored once a minute under ambient conditions to establish a stable baseline prior to chemical exposure for 10 min. Then, the tag was exposed to the chemical analyte by either a) placing the lid on a jar with saturated vapor ($H_2O_2/H_2O$ or $H_2O$) or b) in a ziploc bag containing established atmosphere. During the chemical exposure, the tag not accessible to monitoring with a multimeter, but it could still be interrogated with the smartphone at 1-min intervals. Once exposure was complete, the tag was removed from the container and allowed to recover under ambient atmosphere. During this time, $R_s$ and readability were monitored at 1-min intervals.

Binary Logic for Chemical Discrimination Using Arrays of CARDs

FIG. 21 Graph E correlates the binary output of tag readability by the phone ("on" and "off") with the identity of four chemical vapors used in this study. A binary (0 and 1) assignment can be employed in which the presence of a vapor is denoted as "1" and the absence of a vapor is denoted as "0". For example, four unique tags (n=4) can be employed, each programmed for a specific analyte or as a negative control. Because each tag has a unique identification number, the change in readability of each tag in response to a specified analyte is intrinsically linked to the identity and surmounted threshold of the vapor. The n sensor tags can be arbitrarily arranged into a sequence to provide an n digit code (### . . . ) that can be used to identify unique gases and vapors. Using this coding scheme, four types of tags (CARD-1A, -1C, -2, and -3), and three types of vapors ($NH_3$, $H_2O_2$, cyclohexanone), SGS4 can correctly identify the presence of 35 ppm $NH_3$ as '1000', the presence of vapor of 35% $H_2O_2$ dissolved in water as '0100', and the presence of 335 ppm cyclohexanone as '0010.' As one of the most commonly encountered interferents, the presence of $H_2O$ vapor would not invoke a response from the sensor tags employed in this study ('0000'). To enable a 4-bit depth measurement, four individual CARDs need to be placed on a surface. The CARDs employed in this study cover an area of 20.3 $cm^2$ each. Thus, four CARDs, which cannot be stacked on top of each other, would cover an area of 81.2 $cm^2$.

Practical Considerations and Limitations of the Proposed Sensing Strategy

Nine practical considerations and limitations should be taken into account before attempting to implement this sensing strategy: (i) Not all materials are RF transparent. Therefore, the technique can be compromised by the presence of materials that are RF opaque or reflect RF radiation. (ii) CARDs cannot be stacked on top of one-another (please see discussion in Methods under subsection 'Binary Logic for Chemical Discrimination Using Arrays of CARDs'). (iii) Near Field Communication relies on inductive coupling and therefore the technique is sensitive to its magnetic environment. (iv) The technique, as described in the Methods under subsection 'Method for Determining Reflection Coefficient and Readability of CARDs with a Smartphone' is sensitive to the relative orientation of and distance between the smartphone and CARD. (v) Based on the disclosed findings, the 'on/off' threshold is dictated by the amplitude of power transfer between the smartphone and the CARD. Therefore, the make and model of the smartphone may influence the 'on/off' threshold. (vi) Based on the disclosed findings, the "on/off" threshold is dependent on the PENCIL material. (vii) The chemiresponsive materials employed in this study are unprotected from the atmosphere of the laboratory and their performance may degrade over time. (viii) Because the sensing element is exposed, the behavior of the chemiresistor may change abruptly if touched or otherwise disrupted. (ix) This technique is demonstrated in the controlled setting of a laboratory. In a non-laboratory setting, human and environmental exposure to nanomaterials would have to be addressed with packaging around the sensing element.

General Materials and Methods

SWCNTs (purified ≥95% as SWCNT) were kindly provided by Nano-C, Inc. (Westwood, Mass.). 2-(2-Hydroxy-1,1,1,3,3,3-hexafluoropropyl)-1-naphthol (CAS 2092-87-7) was purchased from SynQuest (Alachua, Fla.). $NH_3$ (1% in $N_2$) was custom ordered from Airgas. All NFC tags used in this study (hereafter referred to generically as "NFC tag") were Texas Instruments HF-I Tag-It 13.56 MHz RFID transponder square in-lays (MFG: RI-I11-114A-01), purchased from DigiKey.

Choice of Tags

This example uses commercially available Texas Instruments HF-I Tag-It Plus Transponder Inlays (TI-Tag) to demonstrate the concept of converting a commercially available NFC tag into a chemical sensor. These tags were chosen based on their chemically robust substrate, absence of protective polymeric coating over the circuitry, commercial availability, and low cost. The electronic circuitry of the unmodified tags is supported via polyurethane glue on both sides of a thin (47 μm), flexible sheet of polyethylene terephthalate, which also serves as a dielectric layer for the capacitor. The circuit comprises an aluminum antenna that serves as an inductor (L), a parallel-plate aluminum capacitor (C), and a silicon-based integrated circuit (IC) chip (R), all connected in parallel, forming an LCR resonant circuit (FIG. 18).

Choice of Analytes

The selective detection of a target chemical analyte is a necessary requirement for any functional ultra-low-cost distributed chemical sensor. This requirement was achieved in a manner that does not employ extensive data analysis or computationally-intensive interpretation, and achieves selectivity towards analytes by harnessing established the properties of chemiresponsive materials. See, Mirica K A, Weis J G, Schnorr J M, Esser B, Swager T M (2012) Mechanical Drawing of Gas Sensors on Paper. *Angew Chemie* Int Ed 51:10740-10745, and Mirica K A, Azzarelli J M, Weis J G, Schnorr J M, Swager T M (2013) Rapid prototyping of carbon-based chemiresistive gas sensors on paper. *Proc Natl Acad Sci USA* 110: E3265-E3270, each of which is incorporated by reference in its entirety. Detection of ammonia ($NH_3$) gas, and vapors of cyclohexanone ($C_6H_{10}O$), hydrogen peroxide ($H_2O_2$), and water ($H_2O$) were targeted as model analytes for the detection of industrial, agricultural, and safety hazards. (i) $NH_3$ is commonly emitted in industrial and agricultural settings and is toxic at relatively low levels (3); (ii) cyclohexanone is a volatile organic compound (VOC), commonly used for recrystallization of explosives, such as RDX (4), that can also aid their detection (5); (iii) $H_2O_2$ can be employed in improvised explosive devices (IEDs), as a commonly employed industrial reagent, and is routinely for sanitization (hospitals).

Choice of Smartphone

An off-the-shelf smartphone was utilized to demonstrate the capability for wireless chemical sensing. This type of detector would be compatible with a highly-distributed network of sensors accessible to a large number of people. In this context, the Samsung Galaxy™ S4 (SGS4) was chosen as the primary NFC-enabled smartphone as a result of two factors: (i) the Samsung's Galaxy series are amongst the most widely distributed "smart" mobile devices in history. (ii) the SGS4 runs on Android, one of the most widely distributed operating systems that supports NFC applications. The demonstrated wireless chemical sensing via NFC is applicable to other NFC-enabled devices (FIG. 3). The NFC chip comprises an antenna for inductive coupling with NFC tags, a transmission module with microcontroller for 13.56 MHz carrier signal generation and tag signal demodulation, as well as embedded and external (Subscriber Identity Module (SIM) card) security elements. When used with unmodified TI-tags, the SGS4 can read tags at ~5 cm standoff distance through solid, non-metallic objects such as paper, plastic, and liquids (FIG. 3).

Choice of Smartphone Application

The 'NFC Reader' (Adam Nyback; 5 Jul. 2013) and 'NFC TagInfo' (NFC ResearchLab; 19 Jul. 2013) applications were used to read the tags, and were freely available from the Google Play™ Store at the time of this report. These applications were chosen because they display the tag's unique identification number without invoking other time- or energy-intensive functions of the smartphone. For the purposes of this study, the tag is considered "on" or "readable" if the unique identification number can be retrieved within 5 seconds or less of holding the smartphone at ~2.5 cm distance away from the tag. Conversely, the tag is considered "off" or "unreadable" if the unique identification number cannot be retrieved under the same conditions.

Instrumental Analysis

The RF signal response of the modified TI-tags and smartphone antennas from 10-20 MHz as well as the smartphone-transmitted radio frequency signal were monitored with a custom-made loop probe connected via a BNC cable to a vector network analyzer (VNA) (Agilent E5061B) by measuring reflection coefficient ($S_{11}$) at 50Ω port impedance and 0 dBm input power (FIG. 24).

Ball Milling

Cyclohexanone sensing material was generated by solvent-free ball milling of SWCNTs with 2-(2-Hydroxy-1,1,1,3,3,3-hexafluoropropyl)-1-naphthol (HFIPN) using an oscillating mixer mill (MM400, Retsch GmbH, Haan, Germany) within a stainless steel milling vial (5 mL) equipped with a single stainless steel ball (7 mm diameter). The milling vial was filled with HFIPN (96 mg) and SWCNTs (24 mg) and the mixture was ball milled for 5 min at 30 Hz.

Fabrication of PENCILs

PENCILs (Process Enhanced NanoCarbon for Integrated Logic) were fabricated by loading powdered sensing material into a steel pellet press (6 mm internal diameter) (Across International Item #SDS6), and compressing the powder by applying a constant pressure of 10 MPa for 1 min using a hydraulic press (Across International Item #MP24A).

Fabrication of Loop Probe

Hollow copper tubing covered in heat-shrink wrap was shaped into a square (5 cm×5 cm) shape and soldered to a BNC adapter. Heat-shrink wrap was placed over the connection point, and was shrunk using a heat gun in a fume hood.

Dilution of Ammonia

Delivery of controlled concentrations of $NH_3$ to the sensing devices placed within a gas chamber was performed using a Smart-Trak Series 100 (Sierra Instruments, Monterey, Calif.) gas mixing system at total flow rates between 0.50 and 10.00 L/min. $NH_3$ was diluted with $N_2$.

Dilution of Vapors

Delivery of controlled concentrations of cyclohexanone vapors to the sensing devices placed within the gas chamber was carried out using Precision Gas Standards Generator Model 491M-B (Kin-Tek Laboratories, La Marque, Tex.). Cyclohexanone was diluted with $N_2$ at total flow rates of 0.25-0.50 L/min.

Gas Chamber

A custom gas chamber was fabricated by inserting two plastic syringes (1 mL, NORM-JECT® (one on either side) in the bottom corners of a Ziploc® bag (1 L) and sealing with electrical tape.

Detection of $NH_3$

Sensor tag data was collected according to the method described above. The sensor tag was kept on the benchtop of a fume hood for 10 minutes, followed by exposure to $NH_3$ in $N_2$ (35 ppm) in a gas chamber for 5 minutes, followed by removal and placement on a benchtop of a fume hood for 10 minutes. This procedure was repeated three more times; after the fourth cycle, the sensor tag was allowed to sit on the fume hood bench top for an additional 10 minutes.

Detection of a Single Exposure of $N_2$ (Negative Control)

Sensor tag data $R_s$ and readability by SGS4 was determined according to the method described above. The sensor tag was kept on the benchtop of a fume hood for 10 minutes, followed by exposure to $N_2$ in a gas chamber for 5 minutes, followed by removal and placement on the fume hood bench top for 20 minutes.

Detection of Single Exposure of $NH_3$

Sensor tag data was collected according to the method described above. The sensor tag was kept on the benchtop of a fume hood for 10 minutes, followed by exposure to $NH_3$ in $N_2$ (4 ppm or 35 ppm) in a gas chamber for 5 minutes, followed by removal and placement on the fume hood bench top for 20 minutes.

Detection of Single Exposure of $C_6H_{10}O$

Sensor tag data was collected according to the method described above. The sensor tag was kept on a benchtop underneath a ventilation snorkel for 10 minutes, followed by exposure to cyclohexanone ($C_6H_{10}O$) in $N_2$ (335 ppm) in a gas chamber for 5 minutes, followed by removal and placement on a benchtop underneath a ventilation snorkel for 20 minutes.

Detection of a Single Exposure of $H_2O_2$

Sensor tag data was collected according to the method described above. The sensor tag was kept on the benchtop of a fume hood for 10 minutes, followed by exposure to $H_2O_2/H_2O$ ($Pe_q$) in a plastic Ziploc® bag containing an open jar of $H_2O_2/H_2O$ (35%) for 5 minutes, followed by removal and placement on the fume hood bench top for 20 minutes.

Detection of a Single Exposure of $H_2O$

Sensor tag data was collected according to the method described above. The sensor tag was kept on the benchtop of a fume hood for 10 minutes, followed by exposure to $H_2O$ (100% humidity in air) in plastic Ziploc® bag containing an open jar of water for 5 minutes, followed by removal and placement on the fume hood bench top for 20 minutes.

Semi-Quantitative Detection of $NH_3$

Figure 28:
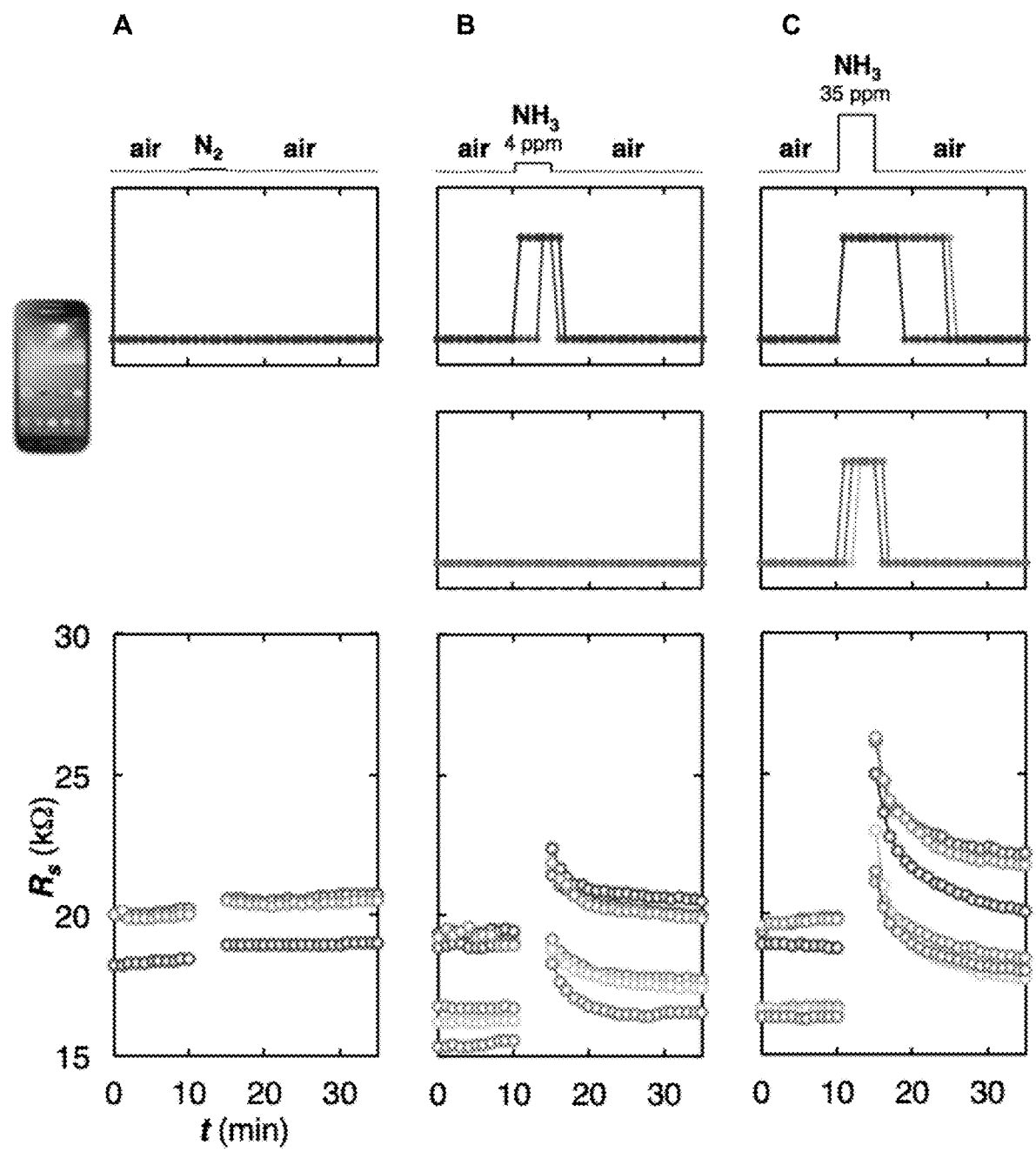
FIG. 28 shows CARD-1B responds to 4 ppm $NH_3$ in $N_2$, but does not respond to pure $N_2$. Graph A shows response of three distinct CARD-1B (dark blue, orange, and red) to a single 5 min exposure of nitrogen as monitored with a SGS4 (top, closed circles) and a multimeter (bottom, open circles). Response of three distinct CARD-1A (purple, yellow, and light blue) and CARD-1B (dark blue, orange, and red) to a single 5 min exposure of 4 ppm $NH_3$ (Graph B) and 35 ppm $NH_3$ (Graph C) as monitored with a SGS4 (top, closed circles) and a multimeter (bottom, open circles).

A sensor tag for 4 ppm $NH_3$ (CARD-1B) was fabricated with $R_s=19.2$ kΩ±0.2 kΩ, and a sensor tag for 35 ppm $NH_3$ (CARD-1A) with $R_s=16.3$ Ωf±0.5Ω. Prior to exposure to NH$_3$ both types of tags were "on" and readable by the phone (FIGS. 20B and 28). Upon exposure to 4 ppm NH$_3$, CARDB-1B turned "off" within one minute of experiencing a change to its local environment, while CARD-1A remained "on". After five minutes of exposure to 4 ppm NH$_3$, CARD-1B had R$_s$=21.9 kΩ+0.4 kΩ (ΔR$_s$=2.8 kΩ+0.4 kΩ); CARD-1A displayed R$_s$=18.8 kΩ+0.3 kΩ (ΔR$_s$=2.6 kΩ+0.1 kΩ). The same type of experiment, with a new batch of CARD-1A and CARD-1B, each fabricated in triplicate, was repeated for 35 ppm NH$_3$ (FIG. 20 Graph B). Under these conditions, CARDs turned "off" (ΔR$_s$=6.0 kΩ+0.5 kΩ): CARD-1B R$_s$ increased to 25.8 kΩ+0.6 kΩ(ΔR$_s$=6.3 kΩ+0.1 kΩ), and CARD-1A R$_s$ increased to 21.9 kΩ+0.8 kΩ (ΔR$_s$=5.4 kΩ+0.8 kΩ), both above the readability threshold.

Determination of Estimated Power Transfer from SGS4 to CARDs

Figure 26:
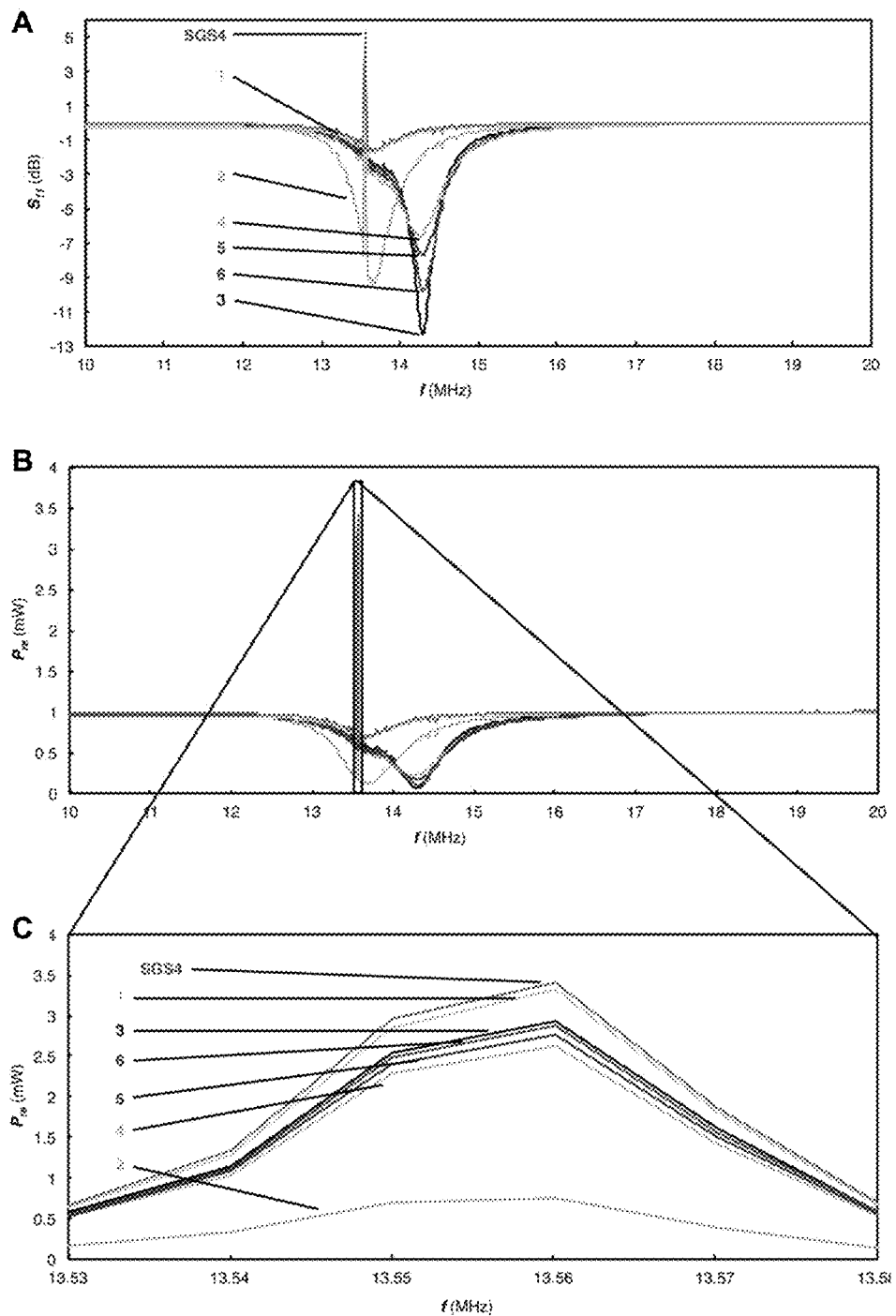
FIG. 26 shows procedure for estimating power transfer from SGS4 to an NFC tag or CARD. Graph A shows reflection coefficient ($S_{11}$) spectrum of SGS4-generated signal (magenta) and spectra of SGS4-generated signal added to spectra of (1) baseline (no tag present), (2) unmodified NFC tag, (3) circuit-disrupted tag, (4) CARD-2, (5) CARD-2 in the presence of cyclohexanone (equilibrium vapor pressure at ambient temperature and pressure) for 5 s, and (6) for 1 min. Graphs B and C show original and magnified spectra, respectively, of estimated power received by the network analyzer corresponding to scenarios depicted in Graph A.

The power transferred from SGS4 to CARD-2 at each stage of fabrication was determined according to a seven-step procedure: (i) collecting S$_{11}$ spectra (n=5) (10 MHz-20 MHz) of the SGS4-generated signal and averaged them into a single SGS4-signal spectrum. (ii) collecting S$_{11}$ spectra (n=5) (10 MHz-20 MHz) of at each stage of modification of a tag leading to the formation of CARD-2. Additionally S$_{11}$ spectra (n=5) (10 MHz-20 MHz) of CARD-2 was collected before and after exposure to saturated cyclohexanone vapor, as described in FIG. 19 Graph A. (iii) averaging the spectra collected in step (ii) into a single spectrum for each tag modification stage and for the gas exposure scenario. (iv) The SGS4-signal spectrum and each spectrum from (iii) was zeroed according to their response at 20 MHz. (v) The zeroed SGS4-signal spectrum from (iv) was added to each zeroed tag and CARD-2 spectrum from (iv) to yield SGS4-tag composite spectra (FIG. 26 Graph A). (vi) The power reflected back to the network analyzer, P$_{re}$, was determined according to Equation 3:

$$S_{11} = 10\log\left(\frac{P_{re}}{P_{in}}\right) \quad (3)$$

Where incident power (P$_{in}$) is 0 dBm (1 µW) (FIGS. 26B and 26C). (vii) The percent power transferred in each case (P$_t$) (FIG. 19 Graph B) was estimated by Equation 4 (FIG. 26 Graph C):

$$P_t(\%) = \left[\frac{\left(\int_{13.53\ MHz}^{13.58\ MHz} P_{re}^{SGS4} df - \int_{13.53\ MHz}^{13.58\ MHz} P_{re}^{x} df\right)}{\int_{13.53\ MHz}^{13.58\ MHz} P_{re}^{SGS4} df}\right] \times 100\% \quad (4)$$

Where x corresponds to scenarios 1-6 described in FIG. 19 Graph A of the main text.

Determination of R$_t$

The "on"/"off" threshold, R$_t$, was estimated (Table 1) by taking the average of the median R$_s$ values found between the "last" R$_s$ correlated with an unreadable CARD and the "first" R$_s$ correlated with a readable CARD, during recovery from a given exposure to analyte.

Other embodiments are within the scope of the following claims.

What is claimed is:

1. A method of detecting a stimulus comprising detecting an output from a radio frequency device having a circuit and including a sensor portion and a chemiresponsive sensor material, the chemiresponsive sensor material closing the circuit, the sensor portion configured to change a detectable property of the circuitry when the stimulus contacts or interacts with the radio frequency device, wherein the detectable property change alters the output of the radio frequency device.

2. The method of claim 1, wherein the stimulus includes an aldehyde.

3. The method of claim 1, wherein the stimulus includes an ester.

4. The method of claim 1, wherein the stimulus includes an alkyl group.

5. The method of claim 1, wherein the stimulus includes a chemical relevant to occupational safety.

6. The method of claim 1, wherein the stimulus includes a mold.

7. The method of claim 1, wherein the stimulus includes an environmental pollutant.

8. The method of claim 1, wherein the stimulus includes light.

9. The method of claim 1, wherein the stimulus includes a biologically relevant analyte.

10. The method of claim 1, wherein the stimulus includes molecules found in a biologically-relevant sample.

11. The method of claim 1, wherein the sensor material include a sensing material selected from the group consisting of a metal, an organic material, a dielectric material, a semiconductor material, a polymeric material, a biological material, a nanowire, a semiconducting nanoparticle, a nanotube, a nanofiber, a carbon fiber, a carbon particle, carbon paste, or conducting ink, organic electronics materials, doped conjugated polymers, inorganic materials, biological molecule receptors, cells, antibodies, aptamers, nucleic acids, functionalized biological molecules, and combinations thereof.

12. A tag for detecting a stimulus comprising a radio frequency device having a circuit and including a sensor portion and a sensor material, the sensor material closing the circuit, the sensor portion configured to change a detectable property of the circuitry when the radio frequency device contacts or interacts with the stimulus, wherein the detectable property change alters an output of the radio frequency device, wherein the sensor portion includes a circuit, and wherein the sensor portion is configured to activate the circuit or deactivate the circuit when contacted or having interacted with the stimulus.

13. A system for detecting a stimulus comprising a radio frequency device having a circuit and including a sensor portion and a chemiresponsive sensor material, the chemiresponsive sensor material closing the circuit, the sensor portion configured to change a detectable property of the circuitry when the radio frequency device contacts or interacts with the stimulus, wherein the detectable property change alters an output of the radio frequency device, and a detector detecting the output from the radio frequency device.

14. The tag of claim 12, wherein the sensor material include a chemiresponsive sensing material selected from the group consisting of a metal, an organic material, a dielectric material, a semiconductor material, a polymeric material, a biological material, a nanowire, a semiconducting nanoparticle, a nanotube, a nanofiber, a carbon fiber, a carbon particle, carbon paste, or conducting ink, organic electronics materials, doped conjugated polymers, inorganic materials, biological molecule receptors, cells, antibodies, aptamers, nucleic acids, functionalized biological molecules, and combinations thereof.

15. The system of claim 13, wherein the sensor material include a sensing material selected from the group consisting of a metal, an organic material, a dielectric material, a semiconductor material, a polymeric material, a biological material, a nanowire, a semiconducting nanoparticle, a nanotube, a nanofiber, a carbon fiber, a carbon particle, carbon paste, or conducting ink, organic electronics materials, doped conjugated polymers, inorganic materials, biological molecule receptors, cells, antibodies, aptamers, nucleic acids, functionalized biological molecules, and combinations thereof.

* * * * *